United States Patent
LeGore et al.

(10) Patent No.: US 7,031,877 B2
(45) Date of Patent: *Apr. 18, 2006

(54) SPECTROSCOPY INSTRUMENT USING BROADBAND MODULATION AND STATISTICAL ESTIMATION TECHNIQUES TO ACCOUNT FOR COMPONENT ARTIFACTS

(75) Inventors: Lawrence J. LeGore, Freedom, ME (US); Robert H. Jackson, III, Veazie, MA (US); Zhong Yu Yang, Old Town, ME (US); Linda K. DeNoyer, Ithaca, NY (US); Peter H. Kleban, Orono, ME (US); Brian G. Frederick, Orono, ME (US)

(73) Assignees: University of Maine, Orono, ME (US); Stillwater Scientific Instruments, Orono, ME (US); Spectrum Square Associates, Inc., Ithaca, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/924,282

(22) Filed: Aug. 23, 2004

(65) Prior Publication Data

US 2005/0086026 A1  Apr. 21, 2005

Related U.S. Application Data

(63) Continuation of application No. 10/165,852, filed on Jun. 7, 2002, now Pat. No. 6,782,342.

(60) Provisional application No. 60/296,850, filed on Jun. 8, 2001.

(51) Int. Cl.
*G06F 19/00* (2006.01)
*G01B 9/00* (2006.01)

(52) U.S. Cl. .................. 702/181; 250/282; 250/287

(58) Field of Classification Search ........... 702/22, 702/23, 24, 25, 26, 28, 32; 324/71.3, 71.4, 324/71.1; 250/222.2, 227.21, 227.23, 281, 250/282, 287, 252.1; 356/300, 303, 326, 356/335, 336, 337, 450, 451
See application file for complete search history.

(56) References Cited

U.S. PATENT DOCUMENTS 5,355,083 A * 10/1994 George et al. .............. 324/229

(Continued)

FOREIGN PATENT DOCUMENTS

WO   WO98/08244   2/1998

OTHER PUBLICATIONS

F.M., Fernández, et al., "Effect of Sequence Length, Sequence Frequency, and Data Acquisition Rate on the Performance of a Hadamard Transform Time-of Flight Mass Spectrometer," *J. Am. Soc. Mass. Spectrom.*, 12:1302-1311 (2001).

Primary Examiner—Patrick J. Assouad
(74) *Attorney, Agent, or Firm*—Hamilton, Brook, Smith & Reynolds, P.C.

(57) ABSTRACT

A spectroscopy instrument that uses spectra produced from random binary sequence modulated data. Statistical estimation techniques are used to achieve resolution enhancement, while properly accounting for the Poisson noise distribution and other artifacts introduced by a modulator or "chopper" or other system components. Indeed, a resolution similar to that of modern spectrometers can be achieved with a dramatic performance advantage over conventional, serial detection analyzers. Both static and dynamic behaviors are theoretically or measured experimentally accounted for in the model as determined. In one embodiment, the finite penetration of the field beyond the plane of the chopper leads to non-ideal chopper response, which is characterized in terms of an "energy corruption" effect and a lead or lag in the time at which the beam responds to the chopper potential.

12 Claims, 20 Drawing Sheets

U.S. PATENT DOCUMENTS

| | | | |
|---|---|---|---|
| 5,396,065 A * | 3/1995 | Myerholtz et al. | 250/287 |
| 5,541,510 A * | 7/1996 | Danielson | 324/233 |
| 5,719,392 A | 2/1998 | Franzen | |
| 6,160,256 A * | 12/2000 | Ishihara | 250/287 |
| 6,198,096 B1 * | 3/2001 | Le Cocq | 250/287 |
| 6,271,917 B1 * | 8/2001 | Hagler | 356/310 |
| 6,300,626 B1 * | 10/2001 | Brock et al. | 250/287 |
| 6,437,325 B1 * | 8/2002 | Reilly et al. | 250/252.1 |
| 6,455,845 B1 * | 9/2002 | Li et al. | 250/287 |
| 6,591,121 B1 * | 7/2003 | Madarasz et al. | 600/310 |
| 6,647,347 B1 * | 11/2003 | Roushall et al. | 702/75 |
| 6,664,545 B1 * | 12/2003 | Kimmel et al. | 250/396 R |
| 6,683,299 B1 * | 1/2004 | Fuhrer et al. | 250/287 |
| 6,782,342 B1 * | 8/2004 | LeGore et al. | 702/181 |
| 6,870,157 B1 * | 3/2005 | Zare | 250/287 |
| 2003/0010907 A1 * | 1/2003 | Hayek et al. | 250/281 |
| 2004/0144918 A1 * | 7/2004 | Zare et al. | 250/287 |
| 2004/0183007 A1 * | 9/2004 | Belov et al. | 250/287 |
| 2005/0001163 A1 * | 1/2005 | Belov et al. | 250/290 |
| 2005/0006577 A1 * | 1/2005 | Fuhrer et al. | 250/287 |

* cited by examiner

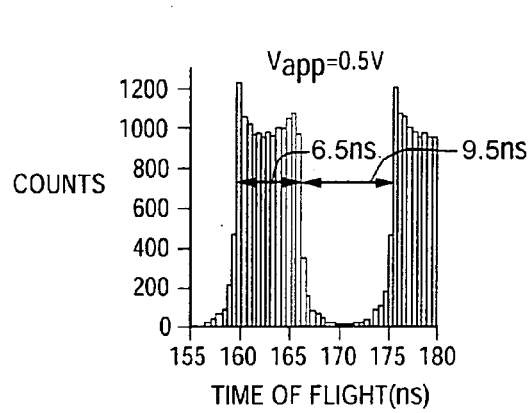
FIG. 12A
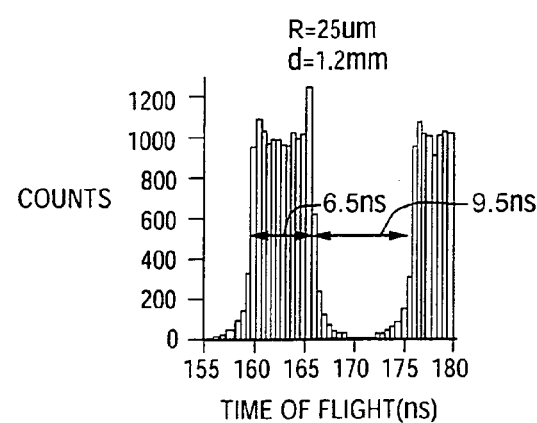
FIG. 12D
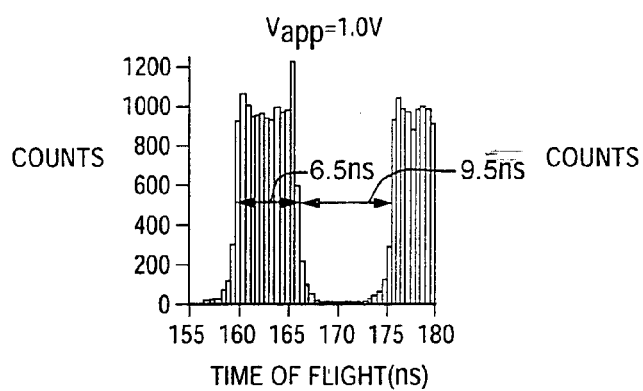
FIG. 12B
FIG. 12C
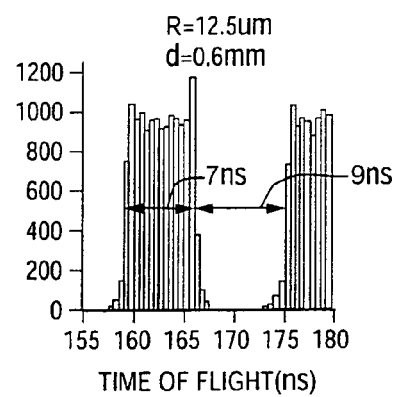
FIG. 12E
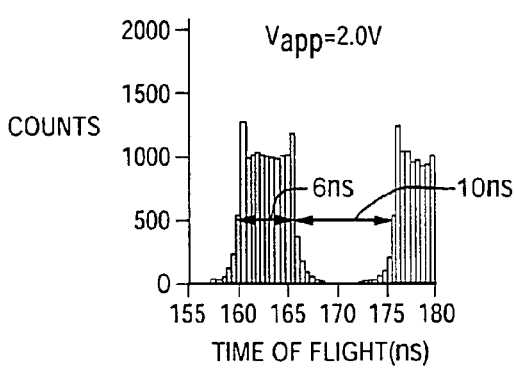
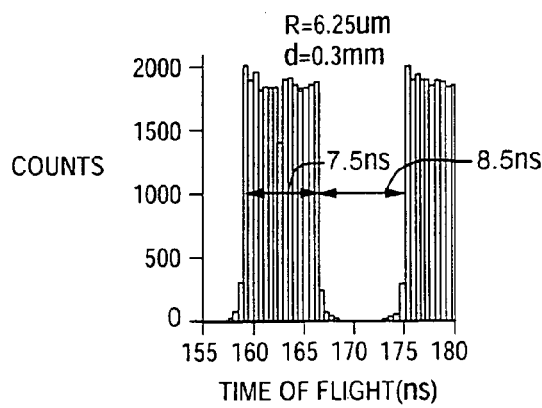
FIG. 12F

SPECTROSCOPY INSTRUMENT USING BROADBAND MODULATION AND STATISTICAL ESTIMATION TECHNIQUES TO ACCOUNT FOR COMPONENT ARTIFACTS

CROSS REFERENCE TO RELATED APPLICATIONS

This application is a continuation of U.S. application Ser. No. 10/165,852, filed on Jun. 7, 2002 now U.S Pat. No 6,782,342, which claims the benefit of an earlier filed U.S. Provisional Patent Application No. 60/296,850 filed Jun. 8, 2001, entitled "Method for Enhancement of Electron Spectrometer Operation Using Maximum Likelihood Spectral Estimation Techniques", the entire contents of which are hereby incorporated by reference.

BACKGROUND OF THE INVENTION

Despite dramatic advances in the energy resolution and throughput of electron monochromators for high resolution electron energy loss spectroscopy (HREELS), a major limitation of conventional, dispersive sector, electron energy analyzers is that they are inherently serial devices, leading to long data acquisition times. The advantage of higher resolution leads to trade-offs in performance (throughput) because channel step size must be reduced, and therefore increasing the number of channels required to measure a given spectral region. Using a multi-channel plate detector to ameliorate this problem is one possibility. Indeed, time-resolved HREELS measurements have been demonstrated with a multi-channel plate in the dispersive plane of a conventional analyzer. However, parallel detection can be accomplished in this way only over a limited spectral range without degrading resolution. Thus, development of an analyzer based upon parallel detection would benefit both typical spectral investigations and allow new experiments to be performed, such as recent inelastic diffraction experiments which are both momentum and energy resolved.

Pseudo-random binary sequences (PRBS), also known as maximal length (ML) shift register sequences and/or pseudorandom noise (PN) sequences, have been used for modulation of photon and particle beams in widely used time-of-flight (TOF) techniques. These find application in, for example, neutron scattering, molecular beam scattering, and ion mass spectroscopy. The PRBS-TOF method achieves a throughput advantage over single pulse TOF due to the 50% duty cycle. PRBS modulation has been combined with TOF-MS, for example in a paper by Brown, W. L., et al., "Electronic sputtering of low temperature molecular solids," in Nuclear Instruments and Methods in Physics Research, Vol. B1, 1984, pp. 307–314. In this example, an incident ion beam was pulsed with a pseudo-random sequence. The ion beam impinged upon a condensed water matrix sample, sputtering or producing secondary ions and neutrals which are measured in a time-of-flight detector. An electron impact ionizer was used to ionize the neutral and then a quadrupole filter was employed to mass select the products. Thus, in this case, the TOF technique was used to measure the energy distribution. To improve the signal-to-background ratio, PRBS modulation and cross-correlation recovery techniques were used, assuming that the source modulation was ideal.

More specifically, in such approaches, the underlying TOF spectrum (the object spectrum, o) is modulated with the PRBS sequence, p, resulting in a periodic, time sequence that is assumed to be defined mathematically as, $(p \otimes o)$. In the standard cross-correlation recovery method, an estimate of the TOF spectrum, r, is obtained by correlating the detected TOF signal data with the PRBS modulation sequence, p: $r = p \oplus (p \otimes o)$. Here, $\otimes$ and $\oplus$ denote convolution and correlation, respectively.

A special property of maximal length PRBS sequences is that the autocorrelation of the discrete binary sequence p is a substantially a delta function; therefore, the recovered spectrum, r, is substantially identical to the original object spectrum, o. In reality, the modulation function p is continuous, but r is an estimate of o as long as the time base (minimum pulse width) of the modulation function is small compared to the linewidth of the narrowest features in o. If this is not the case, then the throughput advantage is gained at the expense of resolution in the recovered spectrum, and over-sampling of the modulated signal, $(p \otimes o)$, leads to a recovered spectrum which is the autocorrelation $(p \oplus p)$ (roughly, a triangular pulse) convoluted with the object function: $r = (p \oplus p) \otimes o$.

In fact, the modulation of the particle beam, whether performed at the source, with a spinning disk type of mechanical chopper, or with an electrostatic deflection based device, is at best described approximately as a convolution with the ideal sequence, $(p \otimes o)$. First, the actual effect of the modulating device on the particle beam differs to some extent from the ideal sequence, p. A number of artifacts in the recovered object function, r, are well known in the art, and some types of non-ideal behavior can be corrected through post processing when $(p \oplus p)$ differs from a delta function, such as arises from machining errors in creating the slots in mechanic spinning disks. Second, most modulators do not act in exactly the same manner on different particles in the beam; for example, the finite thickness of spinning disks leads to a velocity dependent modulation function in molecular beam scattering applications. In this case, the assumption of a convolution is not strictly true.

To the extent that the modulation can be described by a convolution, and the actual modulation function, p, is known or can be estimated, the object function may be recovered simply by Fourier deconvolution. In practice, the presence of noise in measured data complicates deconvolution of spectral data in the simplest cases when the instrument function can be described by a single feature.

The deconvolution of a PRBS modulation sequence, in which the data contains multiple overlapping copies of the underlying object function, has not been reported in spectroscopic applications, to our knowledge.

Probability-based estimation methods for recovery of one-dimensional distributions, and for resolution enhancement of one-dimensional spectral data and two-dimensional image data, have been used by astronomers since 1972. (See Richardson, W. H. 1972, "Bayesian-Based Iterative Method of Image Restoration", J. Opt. Soc. Am. 62, 55–59; Frieden, B. R. 1972, "Restoring with Maximum Entropy and Maximum Likelihood", J. Opt. Soc. Am. 62, 511–18; Lucy, L. B. 1974, "An iterative technique for the rectification of observed distributions", Astron. J. 19, 745–754; and Ables, J. G. 1974, "Maximum Entropy Spectral Analysis", Astron. Ap. Suppl. 15, 383–93.) Recent success with iterative maximum likelihood and Bayesian methods has been demonstrated in a paper by Frederick, B. G., et al., entitled "Spectral restoration in HREELS," in the Journal of Electron Spectroscopy and Related Phenomena, Vol. 64/65, 1993, pp. 825. The maximum likelihood result is simply an array, which convoluted with the modulation function, fits the data as well as possible, given the noise distribution. A well known example of this approach is the algorithm reference in the paper by L. B. Lucy. The Bayesian method employed by Frederick, et al., includes a maximum entropy constraint that limits the degree of resolution enhancement in a manner that leads to a single converged estimate with no arbitrary adjustable parameters.

SUMMARY OF THE INVENTION

We have invented an instrument that uses a PRBS particle beam modulator and detector together with a probability based estimation algorithm for removing artifacts introduced by components of the instrument.

Specifically, in a preferred embodiment, an interleaved comb-type chopper can modulate an electron beam with rise and fall times of less than a nanosecond, which corresponds to meV energy resolution for low energy electrons. The finite penetration of the fields associated with this electrostatic device produces certain non-ideal behavior, which we characterize in terms of an "energy corruption" effect and a lead or lag in the time at which the beam responds to the chopper potential.

According to our invention, for the first time, an instrument employs maximum likelihood, maximum entropy, or other probability based estimation methods to recover the underlying TOF spectrum, in spite of the corruption. These methods can be used to undo the corrupting effects of (a) less than perfectly "maximal length" PRBS sequence; (b) specific chopper effects; and (c) in general, detected signal artifacts introduced by components of the instrument.

Compared to the standard cross correlation method, i) the resolution is improved relative to the nominal time base resolution of the PRBS or other modulating sequence; ii) the Poisson (pulse counting) noise is accounted for; and iii) artifacts associated with imperfections of the chopper or other component performance are reduced.

A spectroscopy instrument thus makes use of statistical estimation techniques to account for component artifacts in accordance with the present invention. The instrument may use several different types of physical phenomena to determine the attributes of a sample. In one specific embodiment, a particle source such as ion source provides a stream of particles to a propagation path. The instrument uses a modulator grid or "chopper", driver electronics, and a sequence generator to modulate the ion source. The ion source may be modulated directly either prior to or subsequent to its application to a sample in order to provide a particle beam that is modulated in time.

The modulator may itself take different forms; one particularly useful implementation as a grid of wires. In addition, spinning disk-type modulators can be utilized which encode the specific modulation sequence as a series of holes around the periphery.

Particles of different chemical makeup exhibiting different physical time-of-flight properties thus travel down the propagation path at different times over different distances to arrive at one or more detectors. A time-to-digital converter then provides a signal to a computer to analyze the detected signal to determine the chemical makeup of the sample.

As has been alluded to above, the computer uses a component model that makes use of maximum likelihood estimation. In an implementation of a statistical method that uses a maximum likelihood method, the so-called Lucy algorithm can be used to refine the estimate for the object spectrum. It will be understood by those of skill in the art that other algorithms can be used.

The computer may perform this statistical method as follows. For example, a system response function is first chosen. The system response function may be an a priori measured response, such as the modulated signal measured with a monochromatic source or from a monochromator. It may also be obtained from a theoretical model, or from a set of data measured on the same sample, for example a high resolution single pulse TOF spectrum and a PRBS modulated spectrum. If the single pulse spectrum is a good estimate of the underlying object spectrum, o, then the PRBS modulated data, y, and then an estimation method such as Lucy can be used to obtain p by deconvolution of y with the estimated object spectrum, o.

The computer also obtains an initial estimate, $o_i$, of the object spectrum. This can be from a previous spectrum or from performing a cross-correlation of the modulating sequence with system response data.

The system response and initial object spectrum estimate are then combined with a model of the instrument that may for example include the noise and physical characteristics of the instrument, to select an appropriate probability based estimation algorithm. A refined estimate is then obtained; the estimate obtained may be acceptable as determined by criteria, or iteration via the refinement process may be necessary.

Thus, although PRBS modulation has been known and used in many areas of spectroscopy in the prior art {including neutron scattering, molecular beam scattering, TOF-MS and secondary ion mass spectroscopy (SIMS)}, and although digital signal processing methods for data recovery have been utilized in an even wider range of spectroscopies, we know of no examples in which the actual response function of the system, particularly the modulator, has been estimated and used to directly deconvolute the PRBS modulated data. There are a number of reasons that deconvolution of PRBS modulated data may not have been contemplated in this field. This may have been driven by the fact that the delta-function autocorrelation properties of PRBS sequences were presumed to provide perfect recovery of the underlying spectrum, and that no further artifacts were introduced by the process.

There has in fact been a general skepticism towards deconvolution of one dimensional spectroscopic data, in part due to the difficulty of the inversion problem. The presence of noise in real data leads to artifacts, even when the response function is known accurately. Filtering usually involves adjustment of some arbitrary parameters, such that the estimate obtained is not unique and the results are subjective. Many methods require that assumptions be made about the underlying spectrum, such as the shape and number of peaks. Furthermore, in the case of PRBS modulation, in which the data contains multiple, overlapping copies of the desired object spectrum, it is not obvious, a priori, that i. there is sufficient phase information to allow deconvolution of the data, even for the case in which the response function is known and the data is measured without noise; or ii. that existing algorithms may not converge to the true solution.

There has been an emphasis upon real-time display during data acquisition, such that Fourier transform based instruments did not become popular until Fast Fourier transform algorithms and sufficiently fast computers became available. The iterative methods we have utilized here have required sufficient computational power that real-time processing during data acquisition has been a limitation; nevertheless, dramatic increases in computational power associated with DSP's and FPGA's now allow much more sophisticated processing in real-time.

Unlike traditional non-linear least squares fitting algorithms that optimize typically not more than 15 or 20 parameters, the methods we have chosen require optimization of at least as many parameters as there are points in the modulated time series data. The method makes no assumptions regarding the number or shape of features in the underlying TOF spectrum, except that the spectrum is positive definite. Therefore, the inversion problem appears to be much more difficult than tradition non-linear fitting problems.

A critical factor in our approach is to oversample the data, relative to the PRBS time unit, which is counter prevailing practice in the field. Brock et al, in U.S. Pat. No. 6,300,626 note that "is procedure will increase the definition of individual peaks, but is not able to increase the time or mass resolution of the device." While this is true for the measured time resolution, particularly for a single pulse TOF spectrum, the information content in the signal may be significantly enhanced by oversampling the data and the system response function. In addition to dramatically reducing artifacts in the recovered spectrum due to certain kinds of non-ideal behavior of the modulator, we have demonstrated that a resolution enhancement by a factor of at least 8× can be achieved with PRBS modulation. This is in part due to the square pulse like shape of the response function, retaining relatively high frequency components in the Fourier domain.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 3a is a segment of an ideal $2^8-1$ bit PRBS sequence which is over sampled by a factor of 16 and FIG. 3b its autocorrelation function; FIG. 3c is the effect of a linear rise time on FIG. 3d, the autocorrelation function; and FIG. 3e is the effect of exponential rise and fall times with a duty cycle less than 50% producing artifacts in FIG. 3f, the autocorrelation function. The central section of each autocorrelation function is expanded to show the peak shape.

FIG. 8a shows energy and angular distributions ontained with the conventional analyzer as a function of the applied static potential, $\pm V_{app}$; and FIG. 8b time-dependent response and angular distributions with a TOF detector.

FIG. 11a for 0.25 V; FIG. 11b for 0.5 V; FIG. 11c for 1.0 V; and FIG. 11d for 2.0 v.

FIGS. 12a–c show calculated time-dependent responses as a function of applied voltage, $V_{app}$; FIG. 12a 0.5 V, FIG. 12b 1.0 V and FIG. 12c 2.0 V.

FIGS. 12d–f show this response as a function of wire spacing at constant R/d (i.e. constant transmission) for $V_{app}$=1.0 V. The peaks and tails, due to energy corruption, as well as lag and lead effects, decrease with $V_{app}$ and with d.

DETAILED DESCRIPTION OF A PREFERRED EMBODIMENT

Figure 1:
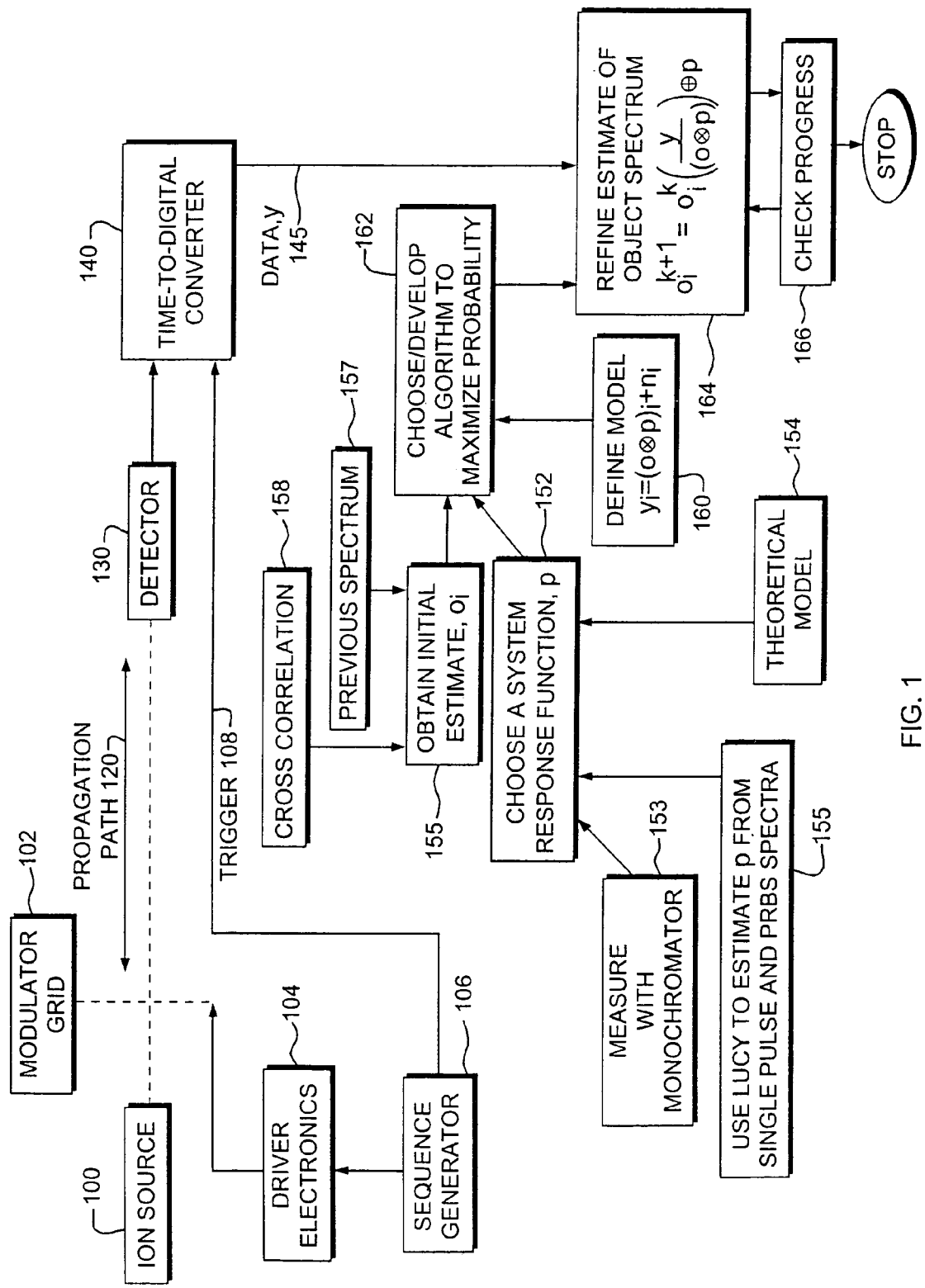
FIG. 1 is a block diagram of components of an instrument constructed according to the invention.

1. Using Statistical Estimation Techniques to Account for Component Artifacts in a Spectroscopy Instrument FIG. 1 is a block diagram of a spectroscopy instrument that makes use of statistical estimation techniques to account for component artifacts in accordance with the present invention. The instrument may use several different types of physical phenomena to determine the attributes of a sample. In general, a particle source such as ion source 100 provides a stream of particles to a propagation path 120. The spectrometer is a type of spectrometer that makes use of a modulator grid or "chopper" 102, driver electronics 104, and sequence generator 106 to modulate the ion source 100. Alternatively, the ion source may be modulated directly either prior to or subsequent to its application to a sample in order to provide a particle beam that is modulated in time.

The modulator 102 may itself take different forms; one particularly useful implementation as a grid of wires is discussed in detail below. In the case of a grid modulator 102, the modulation sequence applied to the modulator 102 may be generated by a shift register, stored in a look-up table or the memory of a digital signal processor or field programmable gate array, etc. In addition, spinning disk-type modulators can be utilized which encode the specific modulation sequence as a series of holes around the periphery.

Particles of different chemical makeup exhibiting different physical time-of-flight properties thus travel down the propagation path at different times over different distances to arrive at one or more detectors 130. A time-to-digital converter 140 then provides a signal to a computer 150 to analyze the detected signal to determine the chemical makeup of the sample.

In accordance with one embodiment of the present invention, a component model 160 that makes use of maximum likelihood estimation or other statistical estimation methods is used to process the detected signal. Shown in FIG. 1 is an implementation of a statistical method that uses a maximum likelihood method, the so-called Lucy algorithm (described in detail below) to refine the estimate for the object spectrum. It will be understood by those of skill in the art that other algorithms can be used.

The computer performs a number of component elements of the instrument as follows. For example, at 152, a system response function is chosen. The system response function may be an a priori measured response, such as the modulated signal measured with a monochromatic source or from a monochromator 153. It may also be obtained from a theoretical model 154. It may also be obtained from a set of data 155 measured on the same sample, for example a high resolution single pulse TOF spectrum and a PRBS modulated spectrum. If the single pulse spectrum is a good estimate of the underlying object spectrum, o, then the PRBS modulated data, y, and then an estimation method such as Lucy can be used to obtain p by deconvolution of y with the estimated object spectrum, o.

At 155 the computer obtain an initial estimate, $o_i$, of the object spectrum. This can be obtained from a previous spectrum 157 or from performing a cross-correlation 158 of the modulating sequence with system response data.

The system response and initial object spectrum estimate are then combined with a model 160 of the instrument that may for example include the noise and physical characteristics of the instrument, to select an appropriate probability based estimation algorithm 162. A refined estimate is then obtained at 164. The estimate obtained may be acceptable as determined by criteria 166, or iteration via the refinement process 164 may be necessary.

Figure 2:
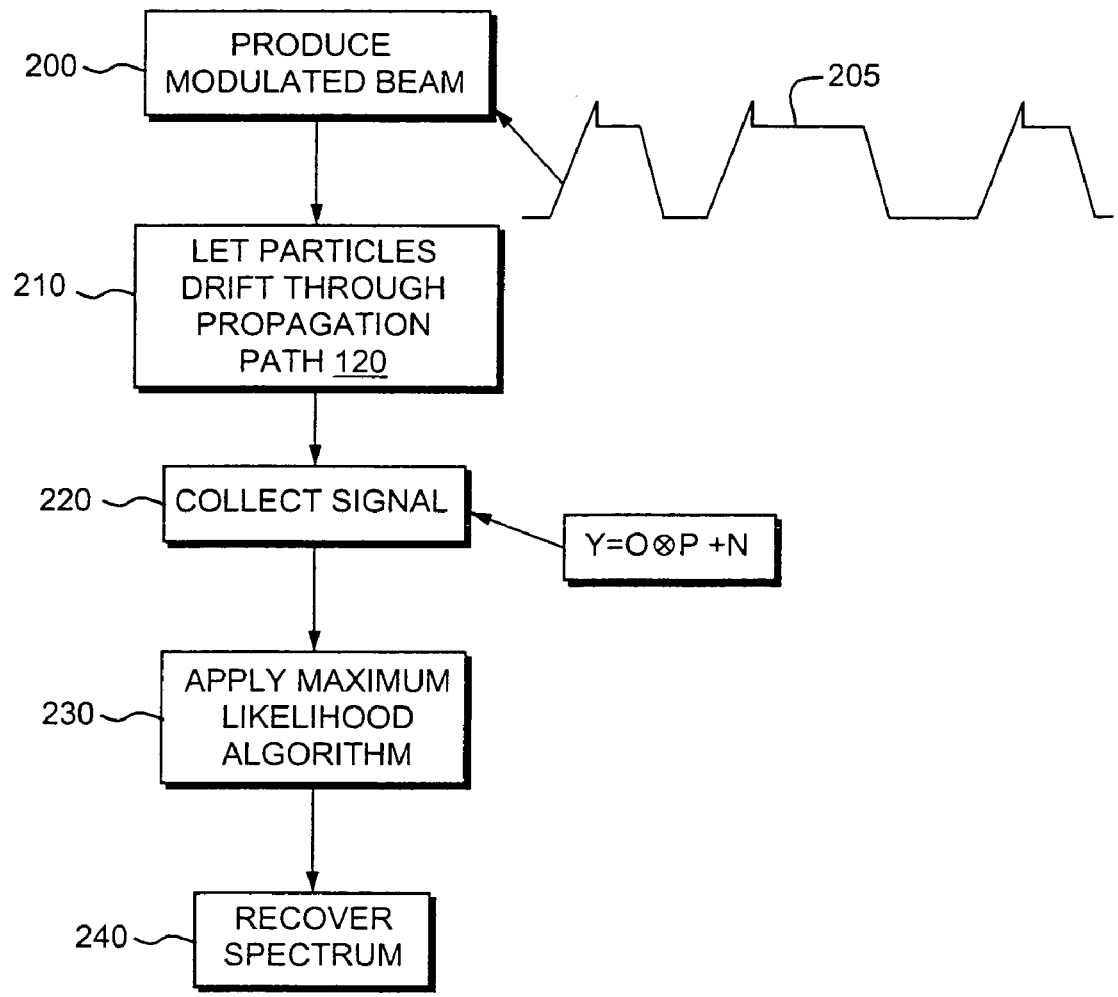
FIG. 2 is a flow diagram of the process steps performed by the instrument.

This embodiment of the instrument can also be thought of as performing a sequence of processes as shown in FIG. 2. These include a first step of producing a modulated beam 205. The modulated particle beam is then allowed to drift through a propagation path in step 210. In step 220, a detected signal is determined based upon particles arriving at the exit point of the propagation path. In a step 230, a maximum likelihood algorithm or other statistical estimation method is applied to the collected signal in order to extract desired information about the original particle beam. This, in turn, allows recovery of the spectrum in step 240.

The model used in the statistical estimation method can account for artifacts introduced by components of the instrument. More specifically, the non-ideal characteristics of the components of the system can include noise in the spectrum due to the nature of pulse counting electronics (Poisson) or in the detector (Gaussian), lead/lag effects in the chopper (modulator), energy spread in the ion beam, second order effects in a linear reflectron that do not completely compensate the energy spread, residual electric and magnetic fields in the flight tube, and the like. We discuss in detail below a model of the effects introduced by a wire grid modulator.

We have found that implementing an instrument with maximum likelihood or other statistical based analysis can be an advantage to a range of different instruments, modulation techniques, propagation path arrangements, and the like.

For example, the specific sequence generated by sequence generator 106 and applied to the modulator grid 102 may be a pseudo-random bit sequence (PRBS) of a so-called maximal length-type, but may also be more generally any sort of sequence that has a relatively broadband spectrum content. By this, we mean that given a fundamental bit period of the modulating sequence, it changes values in such a way to provide frequency content spread across a bandwidth that ranges from two frequencies that depend upon (a) the repetition period of the modulation sequence (the lowest frequency of interest) and (b) the response time of the modulator (the highest frequency of interest). Such a sequence could be obtained in practice, for example, by choosing 1's or 0's by the toss of a coin or by a pseudo random number generator.

Likewise, we have found that the techniques according to the present invention may apply to different types of propagation paths, including dispersive analyzers, as well as time-of-flight detectors, or even mass spectrometers, dispersive elements, such as prisms in Hadamard spectroscopy, or reflectrons used in TOF mass spectrometery, as well as simple flight tubes used in molecular beam scattering, neutron scattering, and charged particle energy or mass analysis.

A maximum likelihood method may be used as the statistical estimation method, using a model of how the object function was converted into noisier data by the components of the instrument and information about the noise distribution. The noise distribution might, for example, be a Gaussian or Normal distribution, or in the case of counting experiments, it might be binomial, which under conditions of rare events, is well approximated by a Poisson distribution.

But the statistical estimation technique can itself be one of several different types of known methods, all of which may be derived from Bayesian probability calculus. Maximum likelihood estimation methods, that optimize the probability of obtaining the data, may be implemented using algorithms such as the Lucy algorithm (also known as the Lucy-Richardson algorithm and the EM algorithm in medical field as described by Shepp and Vardi), and the numerous algorithms described in (Meinel E. S., 1986, "Origins of linear and nonlinear recursive restoration algorithms", *J. Opt. Soc. Am. A.,* 3, 787–799.

Other estimation methods maximize the probability of a result, given the data and other information that is known or assumed about the system, where the result could mean i) a specific model for the system, ii) a specific number or plurality of numbers, such as the intensity of a spectral line or set of lines, iii) a set of parameters that describe the system, or iv) the underlying object spectrum itself. One class of estimation methods that maximize the probability of a result is known as Bayesian methods, and within this class, those that use an entropy expression for the probability of the object spectrum are generally known as maximum entropy algorithms.

Maximum entropy estimation methods, that optimize the Bayesian probability of the object, with specific forms of the a priori probability of the object (such as a combinatorial probability expression), may also be used to obtain an object distribution from the data. Algorithms that implement the maximum entropy optimization include conjugate gradient and other gradient search methods, genetic algorithms, and Monte Carlo methods.

The algorithm for the optimization method can utilize a convolution or a correlation; such computational steps can be carried out with any of a variety of methods, including for example Fast Fourier Transforms, Prime Factor Transforms, serial convolutions, or other techniques. What is important is that the statistical recovery method respect the periodicity of the signal provided to it.

The overall method in the preferred embodiment is preferably an iterative method, although that may not be an absolute necessity in order to obtain certain advantages.

The modulation function applied to the particle beam may also be generalized to any substantially random binary sequence of any length. Some prior art applications have used modulation sequences, but typically these were always PRBS sequences. By lifting this restriction and that of the cross correlation method, we have determined that estimation methods, such as the so-called Lucy-method, work with modulation functions that are not strictly binary. Thus, it should be understood that the modulation function also need not be a strictly binary signal; for example, it might have non-zero or non-100% of expected value transmission values. The application of probability based estimation methods can take into account these attributes of the components of the system and prevent (or minimize) artifacts from appearing in the result estimated.

Indeed, we have determined that for HREELS-type data, a Lucy-type estimation method actually works better with substantially random binary sequence that have only about a 20% duty cycle, rather than the more usual 50% duty cycle restriction associated with maximal length sequences. We have, in effect, determined that an instrument may perform better if the duty cycle of the modulation sequence is actually reduced from 50%.

So far, we have found that if one can use a PRBS Maximal Length sequence, it will provide better results. However, but if for some reason that is not possible (e.g., signal segment lengths of a power of two must be used such as for FFT processing, then there can be an advantage to reducing the duty cycle.

This also implies that the frequency content of the modulation sequence can be "designed." In particular, a truly random sequence would contain a broadband encompassing all frequencies from zero to one-half of the fundamental bit period. However, if it is known that a particular part of the spectrum is of interest in advance, i.e., the mass range of a particular particle is of interest, then sensitivity can be increased in that frequency range by designing the frequency content of the modulation sequence accordingly.

Depending upon the statistical estimation method selected, the computer 150 may also need to obtain an initial estimate. For example, iterative methods such as maximum likelihood and maximum entropy methods typically require an initial estimate for the iteration process. This initial estimate can be obtained by a step of determining a single initial time-of-flight response from the instrument, and storing it. The estimate might be obtained from cross-correlation with the modulation sequence. The estimate might also be derived from a previous estimate obtained from a set of slowly varying time spectra.

Thus, a mode of operation can be included in the instrument that takes sets of modulated data for brief segments of time and then uses that estimate from a one period as an initial estimate for a subsequent or previous segments.

It should be understood that the computer 150 may take a number of different forms, such as a microprocessor, digital signal processor, field programmable gate array, personal computer, array processor, or other processor which is appropriate to the specific intended use of the instrument. For example, handheld instruments are more likely to use FPGAs whereas laboratory instruments might be quite capable of using software-programmed personal computer (PCs) or even array processors.

2. Simulation of a PRBS Modulated TOF Instrument Using Maximum Likelihood Method Recovery Although we have described in this section below a specific simulation that suggests application of a specific "Lucy" maximum likelihood method for a strictly PRBS-type modulated time-of-flight HREELS electron spectrometer, it should be understood that the principles of the invention can be extended to many other types of spectroscopy instruments, modulation sequences, and statistical estimation methods.

Figure 3A:
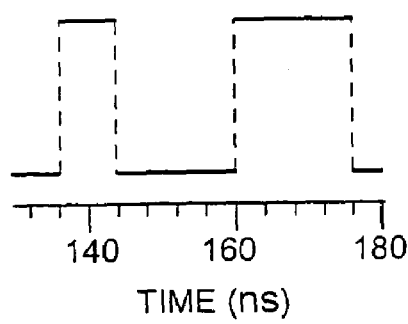
FIGS. 3a–3f are illustrations of the non-ideal chopper response on the autocorrelation functio. Specifically.
Figure 3B:
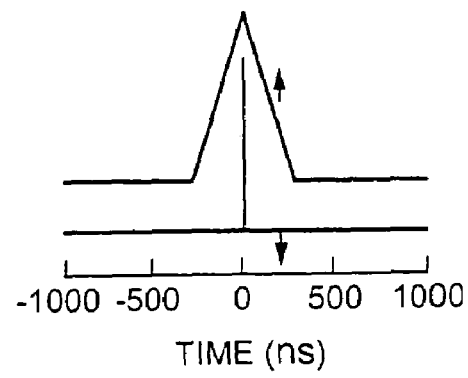
Figure 3C:
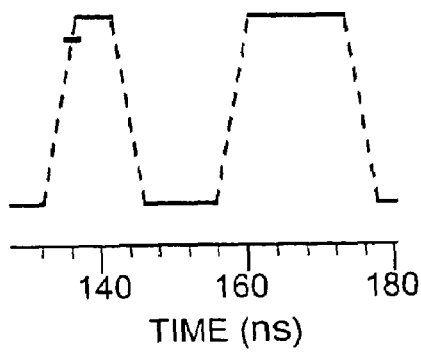

General principals of the PRBS modulated TOF spectrometer will be discussed here prior to presentation of our results. A segment of an ideal PRBS sequence is shown in the curve of FIG. 3a, together with its autocorrelation function in FIG. 3b. If the modulator, or "chopper" is open (1) or closed (0) for the duration of a time step, $\tau$, and the signal over-sampled (here 16×), then the autocorrelation is a triangular pulse with base 2$\tau$. We note that for finite, linear rise and fall times, if the duty cycle is still 50%, as shown in FIG. 3c, the autocorrelation function (FIG. 3d) becomes rounded, but approaches zero smoothly without artifacts.

Figure 4A:
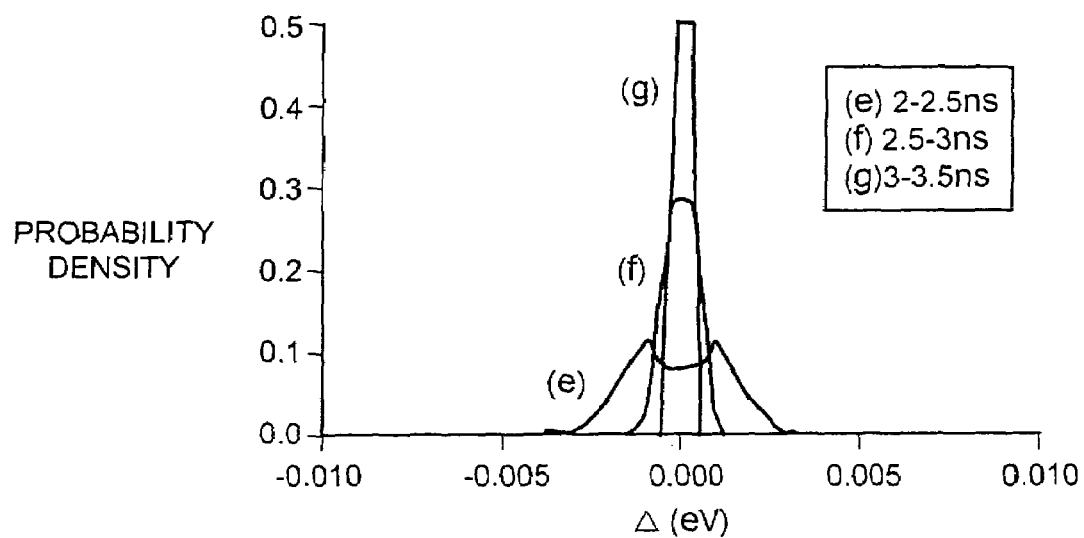
FIGS. 4a and 4b quantify the effect of the finite field penetration on the energy of a charged particle for a chopper known as a Bradbury-Neilsen gate, as a function of the position of particle after the gate at the time the deflection voltages are applied. The information is given in terms of energy corruption histograms for the example of a 2 eV electron. Histograms obtained via a Monte-Carlo sampling of the model potential for 2 eV electrons arriving at the chopper within the time intervals in curve (a) of 0–0.5 ns, curve (b) of 0.5–1 ns curve (c) of 1–1.5 ns, curve (d) of 1.5–2 ns, curve (e) of 2–2.5 ns, curve (f) of 2.5–3 ns, and curve (g) of 3–3.5 ns.
Figure 4B:
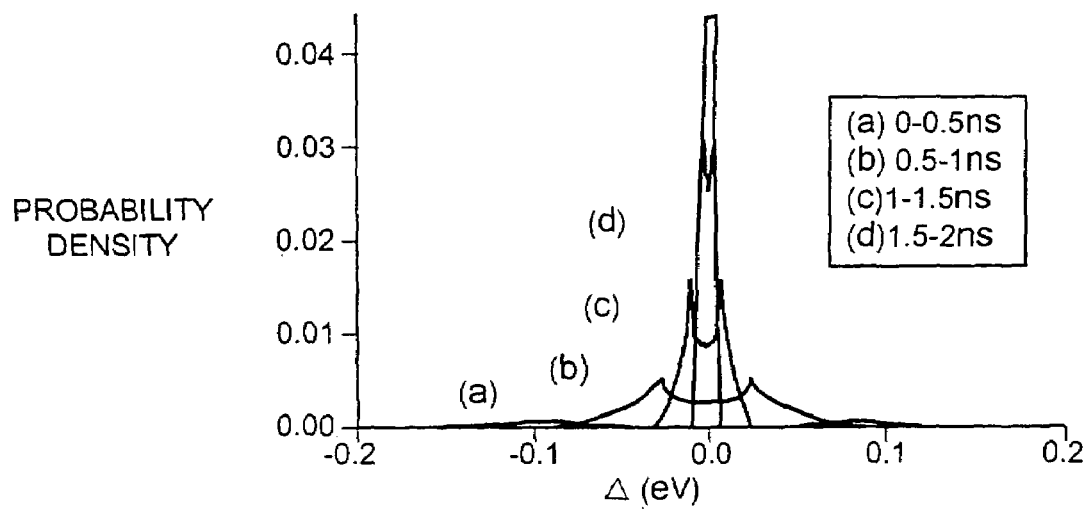

FIGS. 4a and 4b show energy corruption histograms for regions corresponding to the distance traveled in 0.5 ns time steps for a 2 eV electron beam for an interleaved comb chopper with wire spacing of 1.2 mm and radius 25 μm with applied voltages of ±0.4 V and an analyzer acceptance angle of ±1°. From these results, it is clear that the energy corruption is large compared to the energy resolution of modern HREELS monochromators for the first 2–3 ns before or after switching the potentials. Thus, reducing the time base of the PRBS sequence below about 8 ns (for this chopper) significantly degrades the effective resolution of the analyzer for the affected electrons. However, energy corruption is introduced only at the beginning and end of multiple 1's in the PRBS modulation sequence, i.e. when the chopper voltage is changed. There are $2^{n-1}$ edges in a sequence of length $2^n-1$, so the fraction of electrons which pass the chopper un-corrupted depends upon the time base, $\tau$, but is about 50% less than would be the case for a single pulse TOF experiment.

We then prepared a computer simulation of an instrument that defines the chopper response function, p, as the effect of the time-dependent chopper potentials on the detected electron beam current. More precisely, p is the chopper transmission function, $p(t)=I_{det}(t)/I_o(t)$. For the data described here, p is given by a 255 bit ($2^8-1$) PRBS ("maximal length shift register") sequence, with either an ideal step function response, or including one or more of the artifacts described below. Data are typically generated with the PRBS time base of $\tau=8$ ns, and oversampled by factors of 8, 16 or 64, corresponding to detector time bins of 1 ns, 0.5 ns, and 0.125 ns, respectively. A typical HREELS loss spectrum was simulated with a Gaussian elastic peak ($E_p=2$ eV; full width at half maximum (FWHM)=2 meV; 100 kCts/s) and a set of smaller Lorentzian peaks of relative intensity 0.1–10% and FWHM 3 meV, representing inelastic gains and losses. Several doublets, whose separation was greater than or equal to their FWHM, were included to test the resolution enhancement capabilities.

Previous experience with the Bayesian/maximum likelihood algorithms indicates that two peaks must be separated by at least their FWHM to be resolvable.

One asymmetric lineshape and a feature in the tail of the elastic peak were also included to test the ability of the deconvolution algorithms to distinguish overlapping peaks from asymmetric ones.

To generate PRBS modulated, time-series data, (p⊗o), the following procedure was followed. The kinetic energy distribution (energy loss spectrum) was converted into a TOF distribution, o=N(t), with an integer number of counts in each of the discrete flight time bins (note that the object function is defined in the time domain, not the energy domain). A probability function, $f(t')$, was generated by creating a cumulative sum of counts over the array of flight times, $$f(t') = \int_0^{t'} N(t)dt.$$

The probability function, $f(t')$, represents a look-up table, such that a random number chosen over the domain of $f$ implies a flight time, t. To include energy corruption effects, each of the eight energy corruption histograms, corresponding to the seven energy corrupted spatial regions of FIGS. 4a and 4b and the uncorrupted distribution, were convoluted with the original energy distribution before being converted to TOF distributions.

For a beam current of $10^5$ Cts/s, the probability of detecting one electron per PRBS cycle is, from the simulation, $(10^5$ s$^{-1})(255$ bins/cycle×8 ns/bin)=0.2/cycle.

This shows that the noise should obey Poisson statistics and indicates that accumulation over millions of PRBS cycles is required for sufficient signal to noise to recover the object spectrum. Simulated data was produced by cycling through the response function, p, where on each time step, i, p(i) ranged between 0 and 1. If p(i) was greater than a random number between 0 and 1, the gate was "open" and the electron's flight time, t', was chosen randomly from $f(t')$. (Because the probability of selecting any one flight time from the distribution is small, a plot of the variance of the number of counts in each channel, for a single pulse TOF spectrum, was equal to the average count rate in each channel, demonstrating that a Poisson noise distribution was obeyed.)

Then to generate PRBS modulated data, a count was added to the channel corresponding to the flight time plus the position in the modulation sequence, p. If the channel number exceeded the length of the sequence, the value was wrapped around by the PRBS sequence length (8, 16 or 64 times 255). The process was continued, cycling through p until the desired number of total counts was recorded, producing data sets with 2 million to 256 million counts (MCts).

3. Simulation Results of Cross Correlation Vs. Maximum Likelihood Recovery

We also compared the results of the standard cross correlation method with our maximum likelihood deconvolution. The cross correlation method such as that described in Skold, K. et al., Instrum. Methods 63 (1968) pp. 114–116 was performed in MatLab (MathWorks, Inc., 5$^{th}$ ed., Natick, Mass.), resulting in a recovered spectrum, r=(p⊕p)⊗o. A maximum likelihood estimate of the object function, o, was obtained from the modulated data, (p⊗o), using the well known, iterative LUCY algorithm referenced and described previously. The Lucy algorithm maximizes the probability, P(y|o), of obtaining the data, y=o⊗p, given an object function, o, for a Poisson noise distribution:

$$P(y_i|o) = \frac{(o \otimes p)_i^{y_i} \exp\{-(o \otimes p)_i\}}{y_i!}$$

by an iterative process in which the estimate at $o^k$ is used to generate the next estimate, $o^{k+1}$:

$$o_i^{k+1} = o_i^k \left(\frac{y}{(o \otimes p)}\right) \oplus p.$$

For deconvolution of the PRBS modulated data, the initial guess was obtained from the result of the cross correlation method, r, and a prime factor transform was utilized instead of the usual FFT algorithms, since the sequence length is not a power of 2. Because the PRBS modulated data is periodic (edge effects associated with the start of data acquisition are or can be made negligible), no packing of the array is required.

Figure 5:
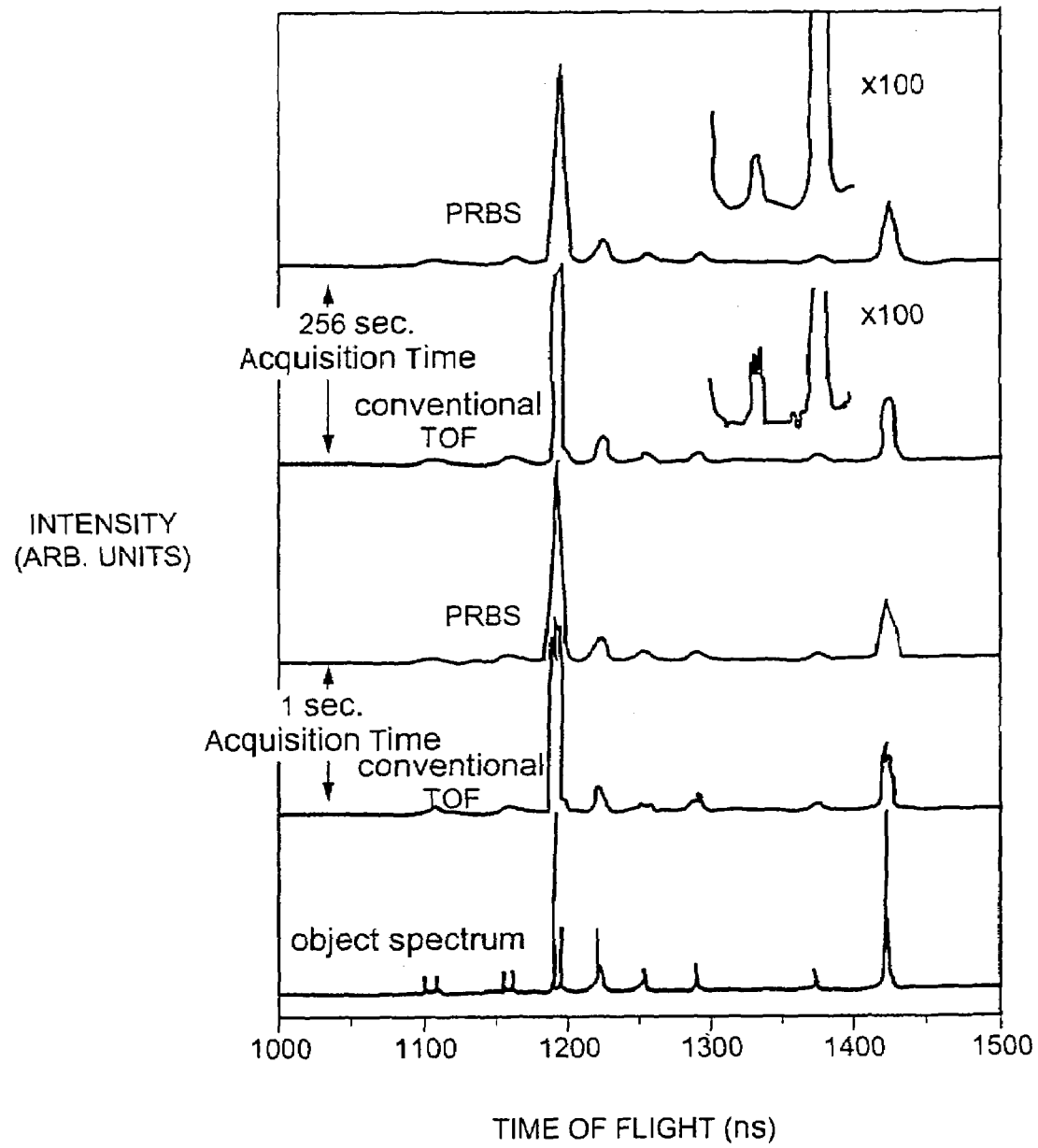
FIG. 5 is a comparison of the object spectrum with simulated single pulse TOF spectra (gate open 8 ns) and the spectra recovered from a PRBS modulated experiment using the cross correlation method. Acquisition times of 1 and 256 sec are shown for an incident beam current of $10^6$ counts/sec. Here, the response function is the ideal (step function) PRBS sequence as in FIG. 3.

Consider first the effects of the Poisson noise distribution on the cross correlation method. FIGS. 5 compares the object spectrum with the spectra from a single pulse TOF experiment (broadened by the 8 ns gate time) and that recovered from a PRBS modulated experiment. The PRBS modulated data was generated using the ideal, step function sequence for p and the object function, o, shown. The single pulse TOF spectrum, generated with a square gate function of 8 ns duration, results in degraded resolution and poor signal/noise compared to the PRBS recovered data. Despite the fact that the cross correlation method is not strictly valid due to the Poisson noise distribution, the method works reasonably well, presumably since the Poisson noise distribution approaches a normal distribution for sufficiently large count rates.

Figure 3D:
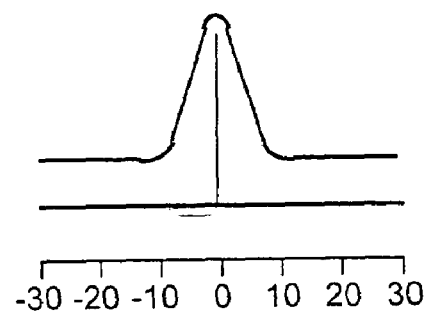
Figure 3E:
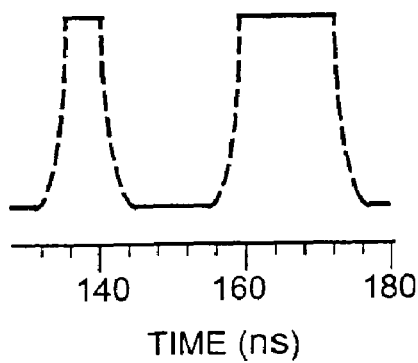
Figure 3F:
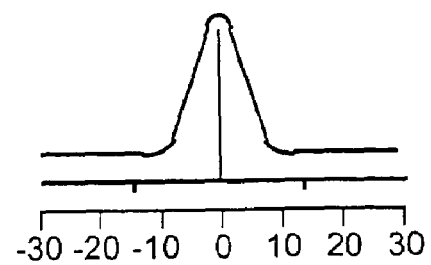
Figure 6:
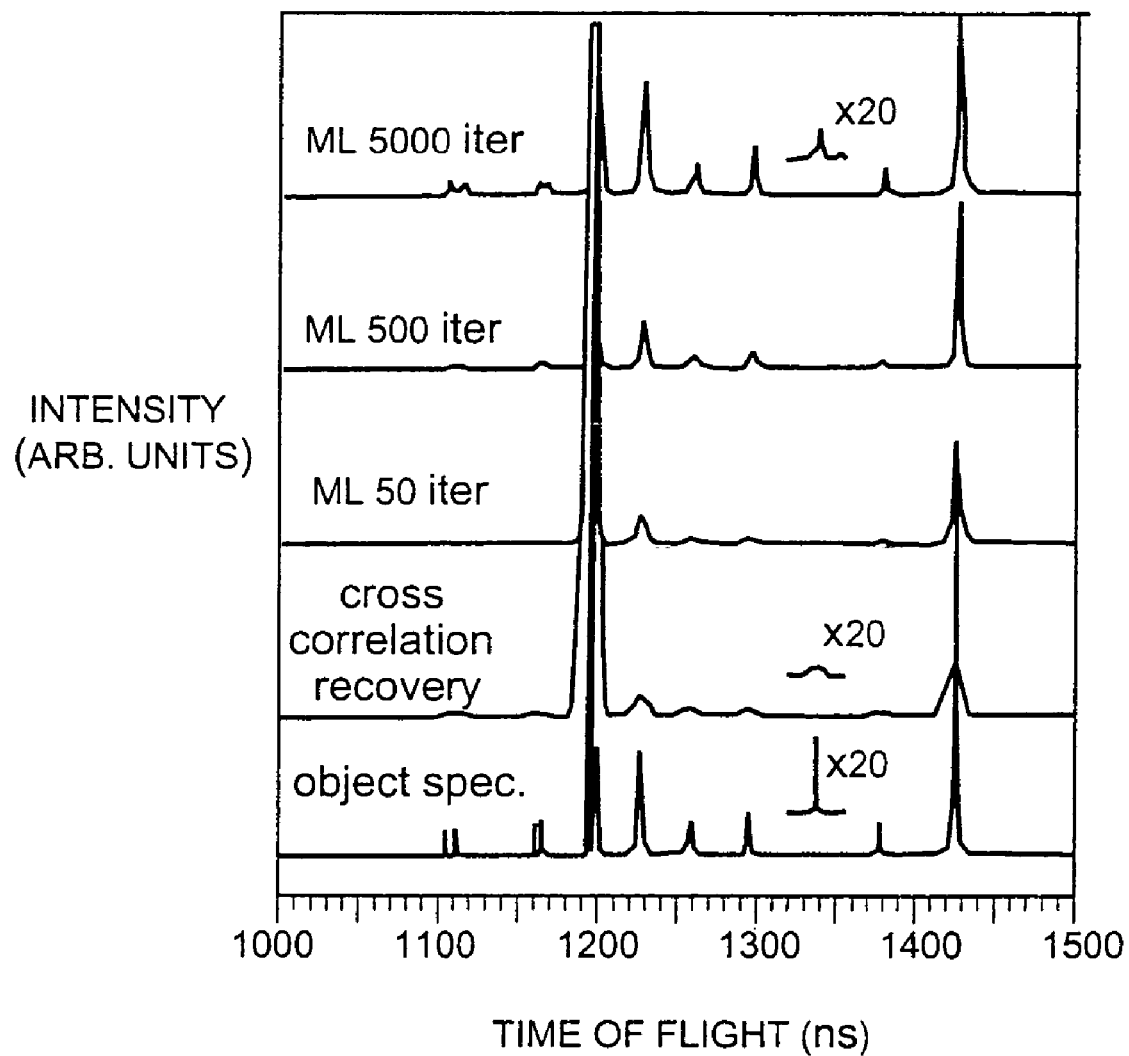
FIG. 6 is a comparison of the object function with estimates recovered from PRBS modulated data using the cross correlation method and the maximum likelihood method (for 50, 500 and 5000 iterations). The modulation function contains linear rise times as in FIG. 3. Data shown for $256 \times 10^6$ counts total in the modulated data.

FIG. 6 compares the results of maximum likelihood recovery with the cross-correlation method. In this example, the modulation function, p, contained linear rise times of 1 ns (c.f. FIG. 5) but maintained a 50% duty cycle. Results given in FIG. 6 are for 256 MCts in the modulated data. The resolution of the cross-correlated spectrum is degraded, as expected, by convolution with an approximately triangular autocorrelation function (c.f. FIG. 3d). In the maximum likelihood recovery method, the results improve with both the total number of counts in the data and the number of iterations. As iterations proceed, the Lucy algorithm refines the spectral estimate, significantly improving spectral resolution, while artifacts remain at a level of less than 0.01%. Note that the gain peaks at 1160 ns, corresponding to 18 meV separation, are clearly resolved.

Finally, we determined the results of maximum likelihood recovery when the modulation function, p, includes both energy corruption effects and the time lags predicted by the model potential for an interleaved comb with applied voltage, $V_{app}=\pm 0.4$ V, wire spacing, d=1.2 mm, radius, R=25 μm and an acceptance angle of $\pm 1°$ (see below for details of this design). The modulation function p, used for deconvolution, was generated in the same way as the data, except that it included only the elastic peak energy distribution. Thus, p characterizes both the monochromator energy distribution and the non-idealities of the chopper, and would be measured in practice simply by directing the monochromatic beam directly into the TOF detector.

Figure 7A:
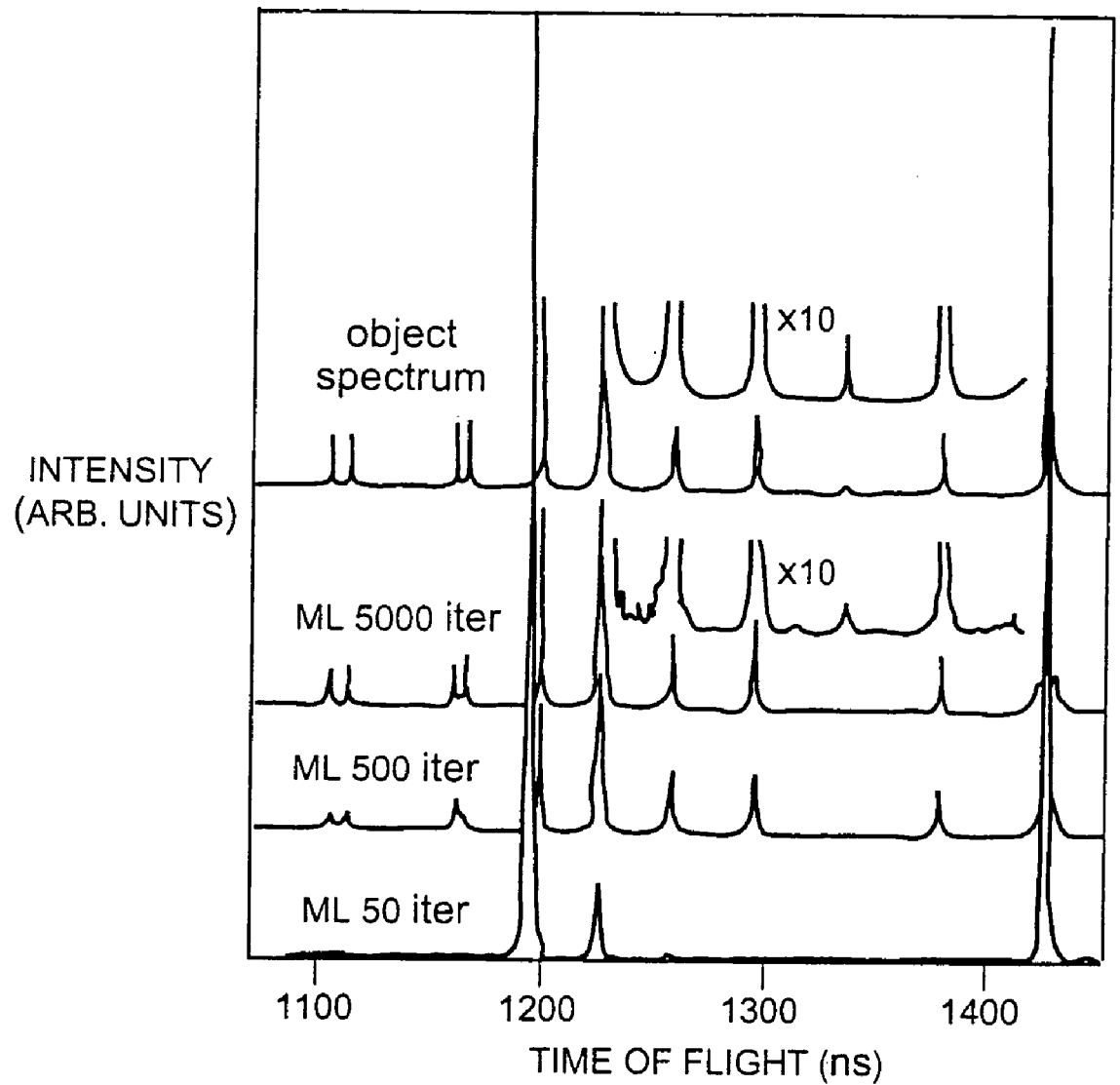
FIG. 7a is a comparison of the object function with estimates recovered from PRBS modulated data that includes the non-ideal chopper response using the maximum likelihood method (for 50, 500 and 5000 iterations). The modulation function contains both energy corruption and the time lag in opening and closing based upon our model of the interleaved comb chopper and the energy distribution of the monochromatic beam. Data shown for $256 \times 10^6$ counts total in the modulated data.

FIG. 7a compares the true object spectrum with results of the Lucy algorithm as a function of the number of iterations. This data was generated with a detector time bin of 0.5 ns, and the reproduction of the object function is excellent. Note that the feature in the base of the elastic peak is well resolved and the resolution of the doublets are comparable to that in the true object spectrum (the doublet at 1230 ns corresponds to 9 meV separation). Even the feature at 1340 ns with intensity 0.1% of the elastic peak is recovered with an intensity roughly an order of magnitude greater than the noise. Thus, the Lucy algorithm is able to account for both the rather substantial energy corruption effects of the chopper and the Poisson noise distribution.

Figure 7B:
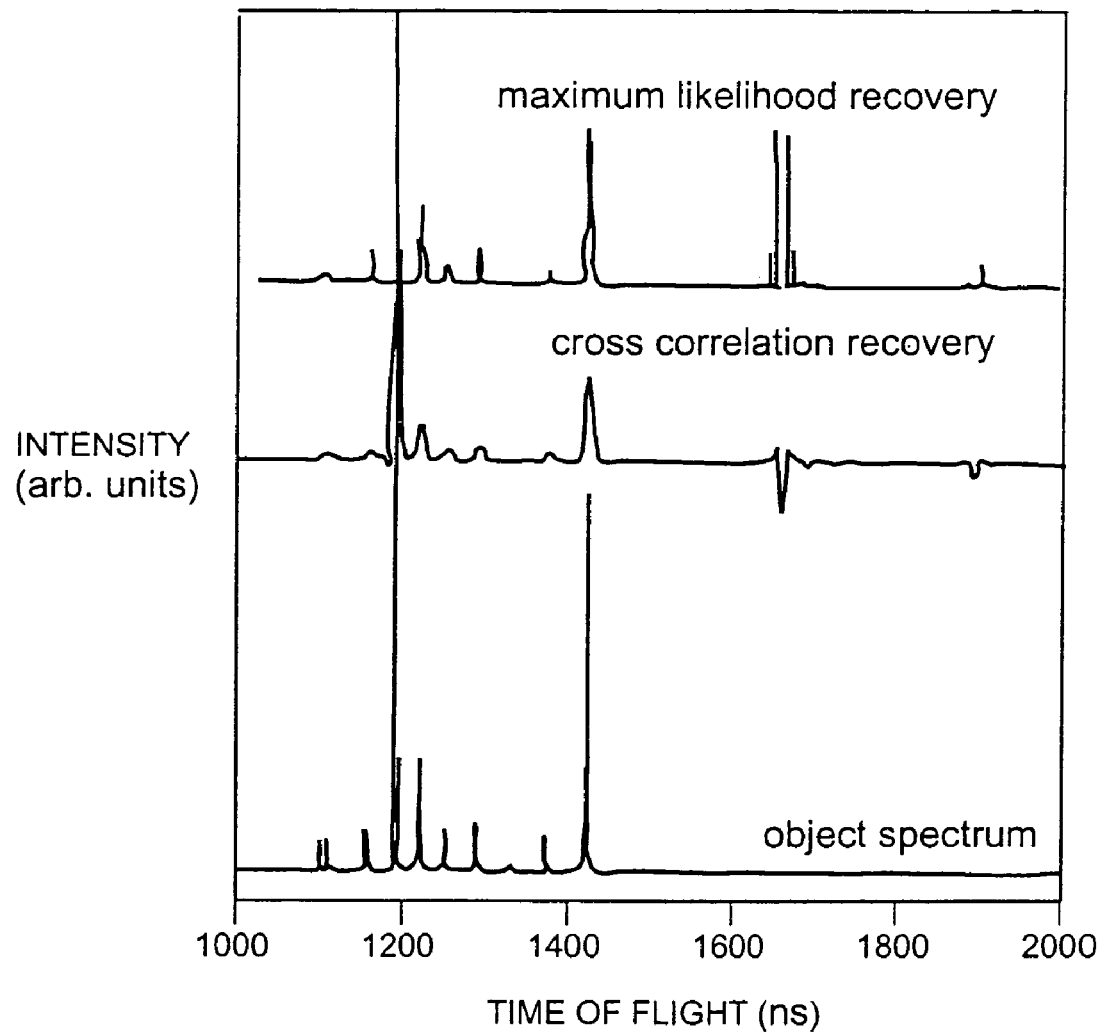
FIG. 7b is an illustration of the negative-going artifacts in the cross correlation recovery due to the non-ideal response of the chopper (middle curve) and the importance of accurately determining the response function: results (upper curve) of using the ideal (step function) PRBS (FIG. 3) sequence in the maximum likelihood method.

By contrast, FIG. 7b shows the cross correlation results using the ideal PRBS response function to process the same energy-corrupted, PRBS modulated data. The negative artifacts appearing between channels 1700 and 1900 ns are consistent with the non-ideal behavior of the chopper, leading to an autocorrelation function similar to that shown in FIG. 5f. To illustrate the importance of accurately defining the modulation function, we also show the results of the maximum likelihood deconvolution using the ideal PRBS (c.f. FIG. 3a) sequence. Artifacts appear at the positions of the negative artifacts in the cross correlation recovery and the true features are split.

We have thus shown for the first time that maximum likelihood methods can be combined with PRBS modulation to achieve resolution enhancement, while properly accounting for the Poisson noise distribution and artifacts introduced by the chopper. The results suggest that resolution similar to that of modern high resolution electron spectrometers can be achieved with a dramatic performance (throughput) advantage over conventional, serial detection analyzers.

4. Modeling an Interleaved Comb Chopper

In our work, we have fabricated choppers using two different methods. The first design utilized a circular, laser-cut ceramic disc with two sets of holes spaced 0.3 mm apart. Tantalum wire (50 μm dia.) was hand wired to achieve 0.6 mm or 1.5 mm spacing between oppositely charged wires. The two distinct wire sets are electrically isolated from one another by the ceramic plate and terminated on each line with a pair of surface mount 100 Ω resistors in parallel. A second type of chopper fabrication used lithographic methods. Gold 50 ohm microstrip leads were patterned onto polished square alumina substrates using the lift-off method. Gold wires were then positioned using a jig to align and tension the wires, which were bonded using a parallel gap welder (UNITEK equipment, UNI Bond (II), Model (50F)). With this method, wire diameters of 25, 50 and 100 μm, centered on inter-wire spacings of 250, 500 and 1000 μm, respectively were achieved. The set of three chopper types, all with 90% transmission, were designed to test the dependence of optical properties on the scale of the device.

We have considered that if the chopper is open or closed for the duration of a time step, τ, and the signal is over-sampled (e.g., 16×), then the autocorrelation is a triangular pulse with base 2τ. We have also determined that for finite, linear rise and fall times, if the duty cycle is still 50%, as shown in curve c, the autocorrelation function (curve d) becomes rounded, but approaches zero smoothly without artifacts.

The problems that arise in applying such a charged particle gate, known as an "interleaved comb" or Bradbury-Nielsen gate, to PRBS modulated TOF mass spectrometry have been recognized by Brock, et. al in Rev. Sci. Instrum. 71 (2000) pp. 1306–1318. We examine here in detail the artifacts that are introduced for electron spectroscopy, and that our statistical estimation method can be used to undo their effects. Three effects can be distinguished:

i) The "dead time" associated with the time for electrons to cross the field affected region leads to an error in the time at which the beam turns on and off. When the PRBS sequence differs from a 50% duty cycle, the autocorrelation function contains oscillations in the baseline and negative artifacts. This effect is analogous to the effects of machining errors and the finite thickness of mechanical chopper disks, used for example in molecular beam scattering. These negative artifacts can be assessed from the autocorrelation of the (imperfect) PRBS sequence, and removed a posteriori, although the effects of the finite disk thickness lead to a velocity dependent error.

ii) The interaction of charged particles with an electrostatic gate causes a change in the energy of the particles when the potentials are switched. The change in energy, which we term "energy corruption", leads to degradation of the information carried by the charged particle, i.e. its energy or velocity, which is the quantity measured in TOF spectrometry. Because the corruption depends upon the position of the electron, relative to the plane of the chopper, at the time the potential is switched on or off, a statistical distribution of energy corruption can be determined directly from the potential for spatial regions as a function of the distance from the chopper.

Figure 8A:
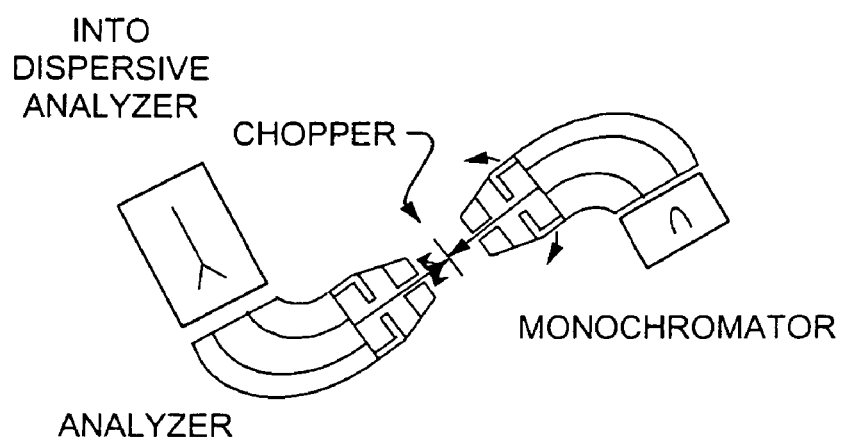
FIGS. 8a and 8b are schematic diagrams of systems designed to characterize choppers. The chopper is mounted on the monochromator at the center of rotation and rotates with it to measure.
Figure 8B:
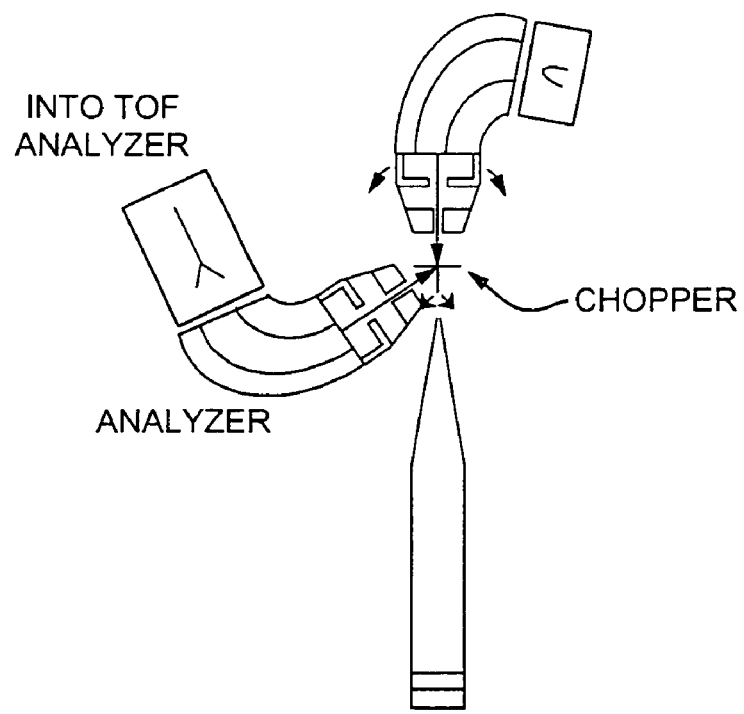

FIGS. 8a and 8b show a schematic diagram of the system designed to characterize the chopper response, based upon an HREELS spectrometer (FIG. 8a) (McAllister Technical Services, Model PS200, Coeur d'Alene, Id.) and a custom designed time-of-flight detector (FIG. 8b). The chopper was mounted at the center of rotation on the face of the monochromator and rotated with it. The electron beam was focused by the monochromator lens through the chopper into the analyzer to characterize the energy (typically 10–20 meV FWHM) and angular (typically ±0.7°) distributions of the incident electron beam. When static potentials were applied to the chopper, the monochromator was rotated by a stepper motor under computer control to measure the angular distribution of the deflected beams. Data acquisition and control were performed using a SPECTRA card (Ron Unwin, Cheshire, UK) customized with a user-written dynamic link library (DLL). When the monochromator was rotated so as to direct the beam into the TOF detector, a modulated signal was applied to the chopper grid and the time-dependent response was measured. The TOF detector was based upon a micro-channel plate detector (AP-TOF, Gallileo Corp., Sturbridge, Mass.) which was custom-modified for negative particle detection.

Figure 9B:
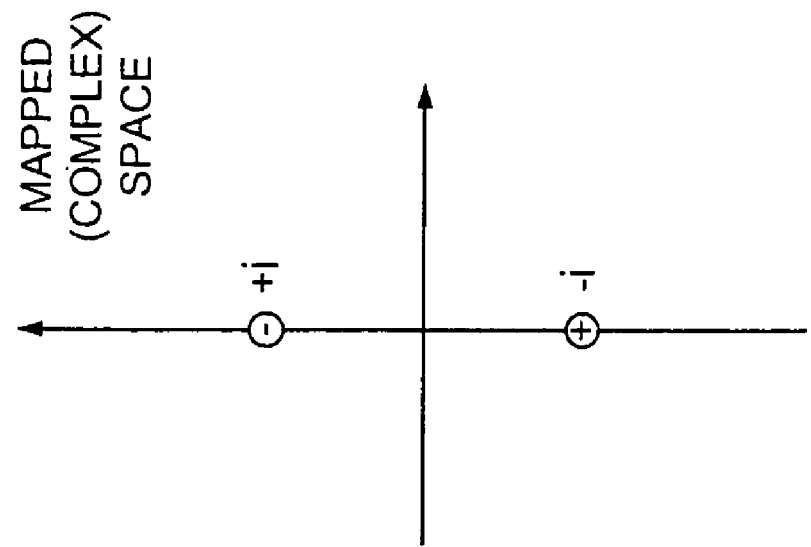
FIG. 9b shows the resulting two-wire problem obtained by conformal mapping.
Figure 9A:
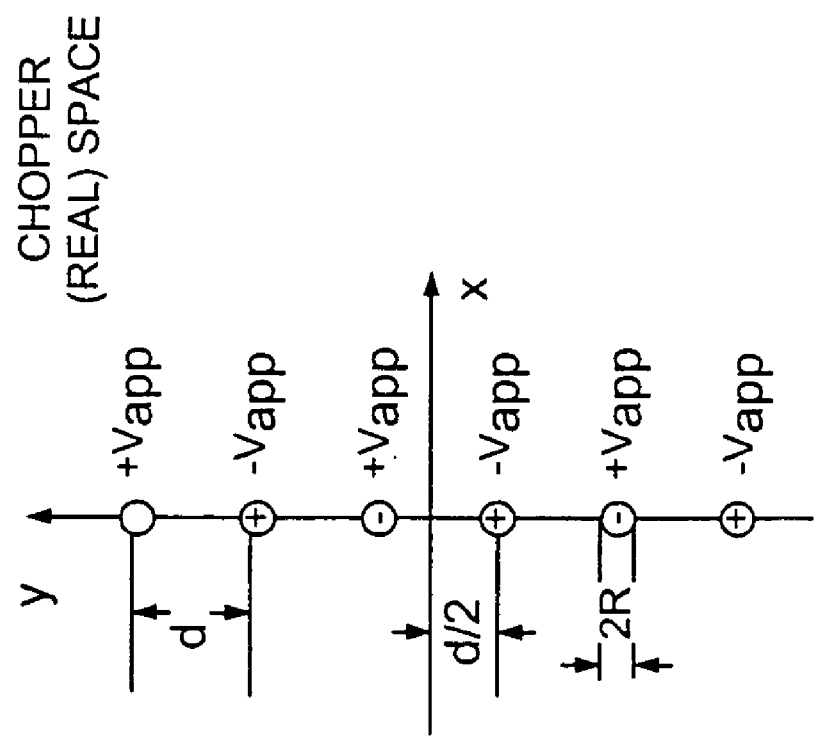
FIG. 9a shows a model for an inifinte array of infinitely long wires of radius, R, and spacing, d, in the x=0 plane with alternating potential $\pm V_{app}$.

We first present a two-dimensional analytical potential, based upon a conformal mapping of an infinite, periodic set of infinitely long, line charges ±λ, onto two line charges, as illustrated in FIGS. 9a and 9b. In real space, wires of diameter 2R and alternating potential, ±$V_{app}$, are spaced along the y-axis with a periodicity, d. Electrons passing in the positive x direction would be deflected in the ±y directions. In real space, let α=x+iy. Using the complex transformation, $$\eta = \exp\left(\frac{\pi}{d}\alpha\right),$$

the line charges alternately map onto the points (0, ±i) in the η space for which the potential is well known. The infinite chopper potential is then $$\psi(x, y) = \frac{\lambda}{2\pi\varepsilon_0} \ln\left[\frac{\cosh\left(\frac{\pi x}{d}\right) + \sin\left(\frac{\pi y}{d}\right)}{\cosh\left(\frac{\pi x}{d}\right) - \sin\left(\frac{\pi y}{d}\right)}\right].$$

The contours of this potential in the real space are nearly circular close to the line charges. Thus, for finite diameter wires with R<<d, i.e. near unity transmission, the line charge solution well approximates the actual chopper potential and we need only choose a point through which the potential passes to define the line charge λ. Choosing the point (x=0, y=d/2−R) to have a potential $V_{app}$ we have $$\lambda = \frac{2\pi\varepsilon_0 V_{app}}{\ln\left[\frac{1 + \cos\left(\frac{\pi R}{d}\right)}{1 - \cos\left(\frac{\pi R}{d}\right)}\right]}$$

The potential (see FIG. 13 below) is simply proportional to $V_{app}$, and has the important feature that it decays as $$\psi \sim 4\lambda \exp\left(-\frac{\pi |x|}{d}\right),$$

such that the potential is reduced to <3% of $eV_{app}$ within the first d spacing, and is <$10^{-5}$ $eV_{app}$ within 3.6 d. For $V_{app}$ of order 1V, the potential for x>3.6 d is small compared to the typical (~2 meV) energy resolution of the monochromatic beam in HREELS.

Trajectory calculations were performed numerically using an adaptive, $4^{th}$ order Runge-Kutta method (MathCad v. 6 and 2000, Mathsoft) with initial positions chosen randomly in a region of negligible potential to the left (x<0) of the chopper plane. The distribution of angular deflection was determined from the final angle after the electron leaves the field affected region ($\psi$<$10^{-5}$ $V_{app}$). To simulate time-dependent changes in chopper potential, trajectories were calculated either in free space or over the applied potential, assuming that the potential was changed instantaneously, until the electron was in a region of negligible potential. For comparison with experimental data, flight times were calculated from the final position and velocity to the detector at a chopper-to-detector distance of 16 cm.

Figure 10A:
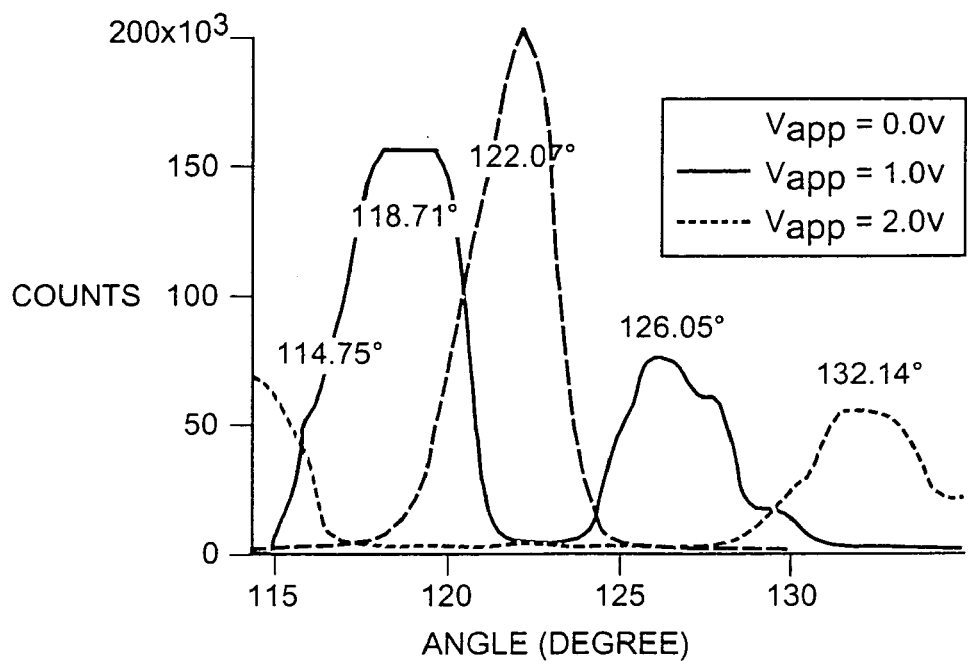
FIG. 10a shows a typical angular distribution, measured with the TOF detector, for a 5 eV beam as a function of the static DC voltage, $V_{app}$, applied to the chopper.

In FIG. 10a, we compare the angular distribution of the deflected electrons as a function of the applied potential using the TOF detector. Similar results were obtained with the dispersive analyzer. For small deflection angles and a beam size large compared to the wire spacing, d, the beam is split into a symmetric distribution, peaked at angles ±$\theta_{def}$, which is approximately linear in the ratio of the applied potential to the electron's kinetic energy, $eV_{app}/KE$. The modulation of the beam is clearly dependent upon both the angular distribution of the incident electron beam and the deflection angle. For an acceptance angle of ±1°, 99.9% modulation is easily achieved under static DC applied potentials. As expected, the deflection angle is independent of the wire d spacing, for constant transmission, or R/d; i.e., as the chopper geometry is scaled to smaller dimensions, the applied voltage must remain constant to achieve the same deflection angle.

Figure 11A:
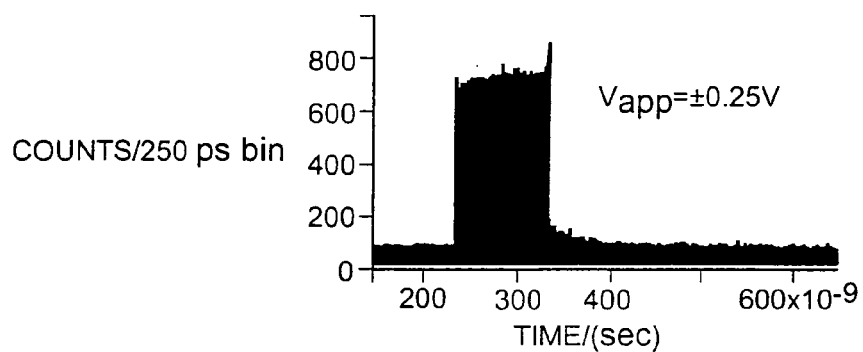
FIGS. 11a–d show the measured time-dependent response of a chopper, with wire diameter, 2R=100 μm, and spacing, d=1 mm, to a 5 eV beam as a function of the chopper potential, $V_{app}$.
Figure 11B:
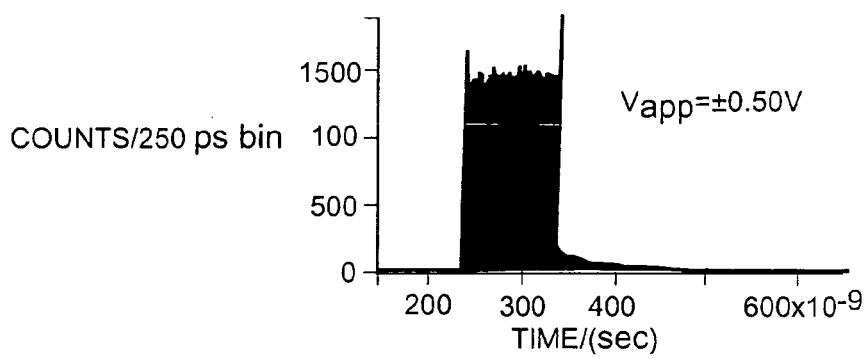
Figure 11C:
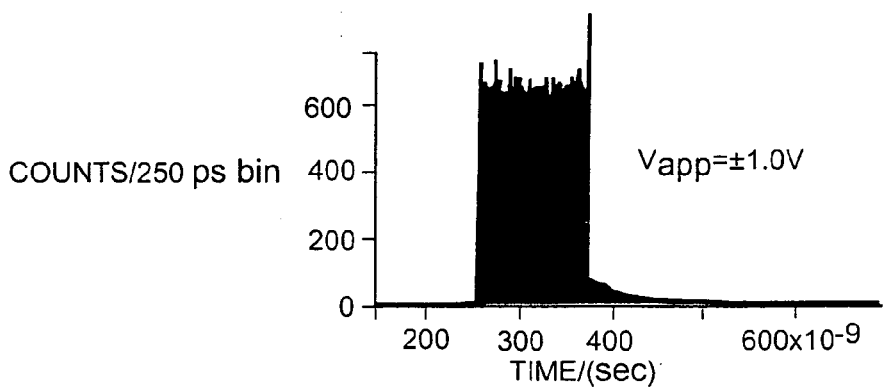
Figure 11D:
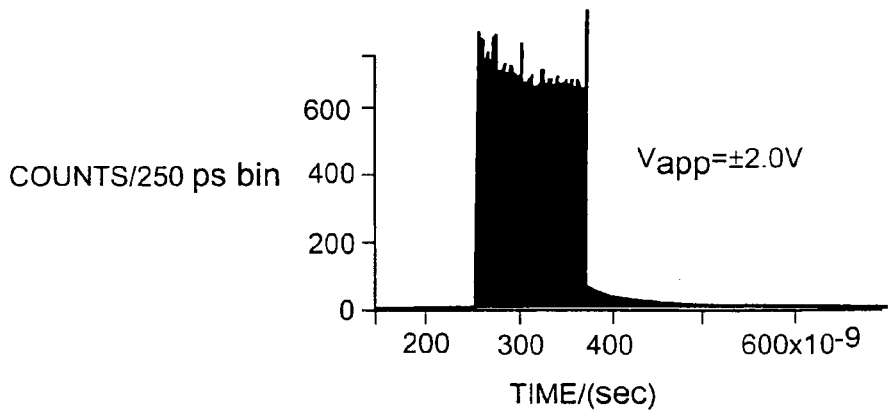
Figure 11E:
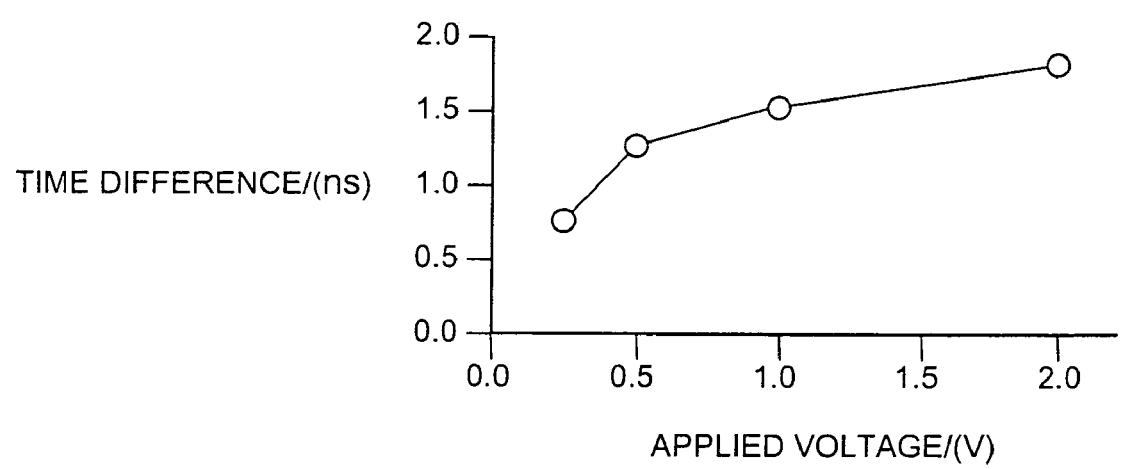
FIG. 11e illustrates the difference between the time that the beam is on the time that the chopper voltages are off.

The time-dependent response, illustrated in FIGS. 11a–11c for the 2R=100 μm chopper, was measured for a range of applied voltages with an incident 5 eV beam having an angular distribution of FWHM=1.5°. The potentials were periodically dropped to zero for approximately 100 ns (period of 700 ns; rise/fall times of 1.5 ns), during which time the undeflected beam was accepted through an aperture of half acceptance angle $\theta_a=1.5°$. The number of counts in each histogram varied with acquisition time, but are shown as counts to allow the noise level to be compared with that expected from the Poisson distribution. The TOF histograms, sampled on 250 ps time bins, show that rise times of <0.5 ns are easily achieved. However, several features of the TOF spectra should be noted. First, the histograms display peaks and tails at the times when the chopper changes state that are significant compared to the Poisson noise distribution. Second, a detailed comparison of the time that the potentials are off and the time that the beam is on shows that the difference varies with applied voltage: the electron beam turns on late and/or shuts off early. The dependence is shown in FIGS. 11a–11c. Third, while the background on the high energy side (shorter flight times) is less than $10^{-5}$ of the average count rate when the gate is open, significant intensity with a distribution to lower energy appears with a relative intensity of $10^{-2}$, which is attributed to inelastic scattering from the relatively thick apertures placed before and after the chopper. The origin of the first two features is discussed in light of the theoretical simulations presented in the following section.

5. Theoretical Simulation Results and Discussion

Figure 10B:
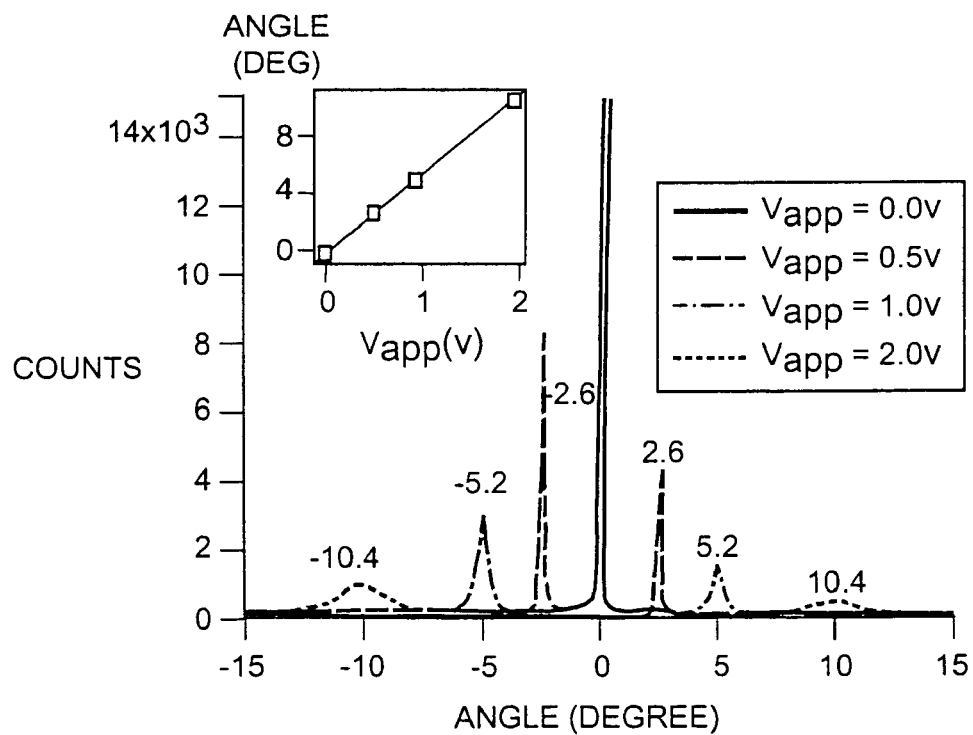
FIG. 10b shows theoretical angular distributions for a uniformly distributed (see text) beam of electrons ($E_p$=5 eV) as a function of applied voltage, $V_{app}$, from trajectory calculations. Inset compares the experimental and theoretical peak deflection angle as a function the ratio $V_{app}$/KE. Wire radius, R=25 μm; wire spacing, d=1.2 mm; flight distance 160 mm; acceptance angle ±1°; angular bin size=0.1°.

We first compare the angular distribution of the transmitted beam (FIG. 10a) with simulations based upon trajectory calculations. Electron positions were chosen randomly within the region (−40 mm<x<40 mm, −1.8 mm<y<1.8 mm). The potentials were applied for the first 8 ns, during which time the first electrons enter the field-affected region. The potentials were then turned off for 8 ns, on again for 8 ns, and finally turned off to calculate the final angle and the time in the field-free flight tube to reach the detector. FIG. 10b shows the angular distributions calculated for the infinite chopper corresponding to the geometry of the ceramic disk design as a function of $V_{app}$. The results show that, for uniform filling of the chopper, the deflection angle in the angular distribution increases proportional to $V_{app}$, and as shown superimposed in the inset of FIG. 10b, agrees quantitatively with the experimental measurements. Whereas the electrons in the simulation have initial velocity parallel to the x-axis, the angular distribution in the experiment leads to broader peaks in the angular distributions of FIG. 10a.

The results of simulations of the time-dependent response are shown in FIGS. 12a–12f. The flight times, for electrons accepted by an aperture of ±1° at a flight distance of 160 mm, are shown as a function of $V_{app}$ in FIGS. 12a, 12b and 12c, and as a function of the wire spacing (for constant R/d) in FIGS. 12d, 12e, and 12f. While the beam is modulated as expected, turning the beam on then off and on again, several features noted in the experimental data are reproduced in the simulations. First, at the transitions, the simulations predict spikes and tails in the histograms which deviate significantly from the Poisson noise distribution. Second, the chopper response (here, the time-dependent beam current) has a lag or lead with respect to the applied voltage making it appear that the gate is open for times less than the 8 ns used in the calculation and closed for times greater than 8 ns. These effects depend upon $V_{app}$ as well as the scale of the chopper (i.e. the wire spacing for constant R/d). Reduction of the applied voltage or reduction of the wire spacing noticeably decreases these effects. We note that late opening and early closing of the gate is analogous to the effect of finite thickness investigated by Zeppenfeld, et al., in Rev. Sci. Instrum. 64 (1993) 1520–1523 for spinning disk mechanical choppers.

Figure 13:
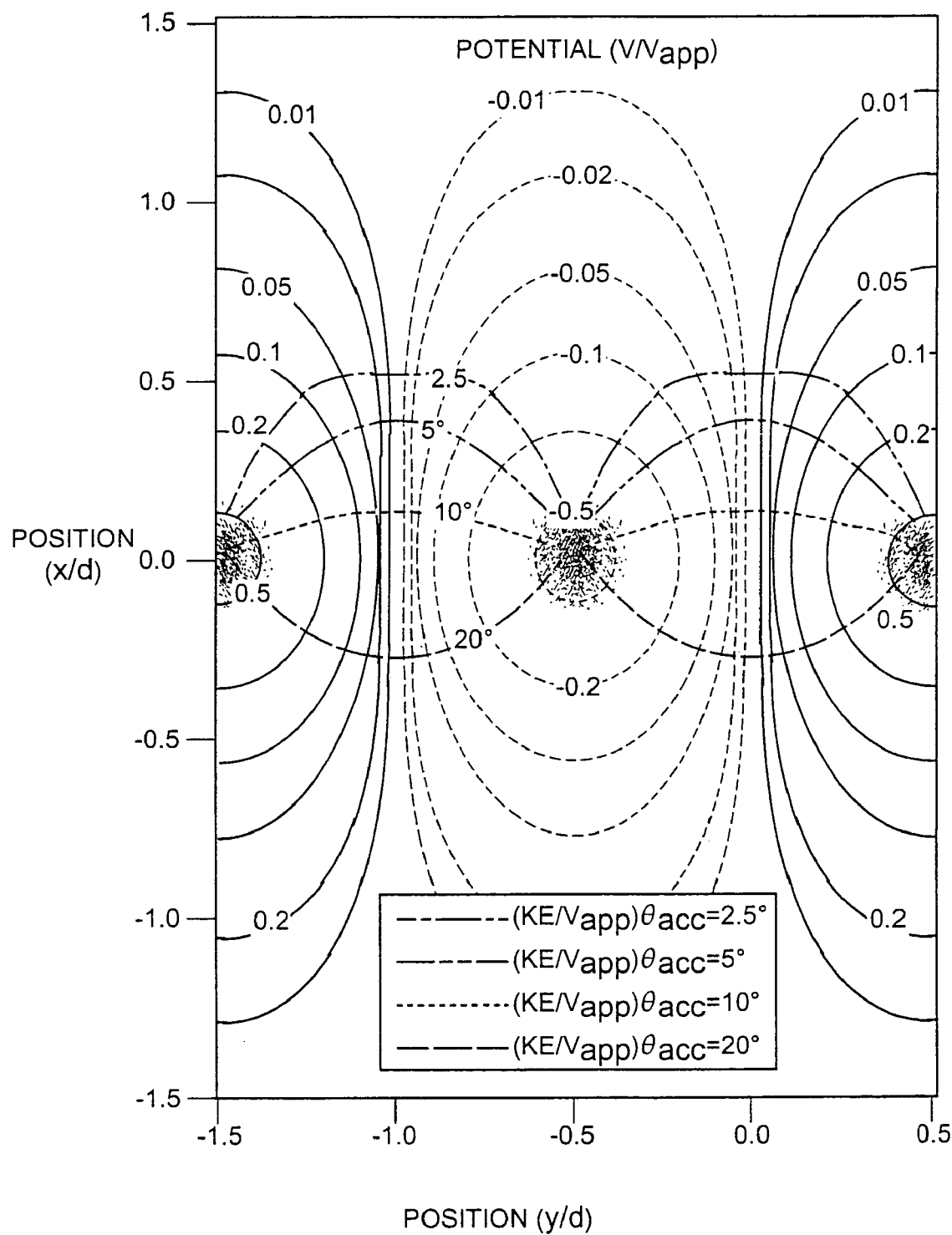
FIG. 13 shows a contour map of the potential, $\psi(x,y)$, with critical boundaries, $f(x,y, \theta_{acc}, V_{app})$, as a function of the acceptance angle and applied voltage. If the electron is at position $(x_0, y_0)$ beyond the boundary at the time when the potential is applied, the electron has final angle $\theta_f < \theta_{acc}$; i.e. the electron reaches the detector, and suffers an energy corruption $e\psi(x_0, y_0)$.

The origin of the spikes and tails can be understood from consideration of trajectories over the potential, shown in FIG. 13. Consider first an electron approaching the chopper with potentials off (gate open). If an electron is near the gate and the potential is applied instantaneously, the electron may gain or lose potential energy, depending upon whether it is closer to a negative or positive wire, respectively. For electrons in the field affected region, it is necessary to compute trajectories to determine whether sufficient transverse field exists over the subsequent path to exclude the electron from the detector. Clearly, this is dependent upon the applied voltage and the acceptance angle of the aperture. The curves in FIG. 13 represent critical boundaries, $f(x,y,\theta_{acc}, V_{app})$, such that if the electron is beyond the curve at the time the potentials are applied, the electron has final angle of $\theta_f<\theta_{acc}$; i.e. the electron reaches the detector. For those electrons which reach the detector, their energy has been changed, or corrupted, by an amount given by the potential at the position of the electron when the potential was changed. Thus, there is a distribution of "energy corruption", ranging from $-V_{app}$ to $V_{app}$. The symmetry of the potential shows that, for a uniformly distributed beam of electrons, the probability of gaining energy is equal to that of losing energy, producing both longer and shorter flight times in the TOF histogram. Therefore, the step function response of the chopper is modified, producing the spikes and tails, which we attribute essentially to these energy corruption effects. As $V_{app}$ is decreased, the maximum energy corruption decreases, and the magnitude of the spikes and tails in the simulations decrease.

The energy corruption effect can be distinguished from a second effect, noted in both the experimental and simulation data, that there may be a lead or lag in the beam current with respect to the times that the potentials are changed. Consider an electron approaching the gate, with $V_{app}=0$, along the mirror symmetry plane, x=0, such that $\psi(x=0,y)=0$. For this trajectory, the energy corruption effect is zero, since the electron is still at zero potential immediately after the voltages are applied. It propagates over some trajectory until leaving the field affected region, where again the potential is zero. However, depending upon the acceptance angle of the detector, the electron may or may not be detected. If the acceptance angle is small, e.g. $(KE/V_{app})$ $\theta_{acc}=2.5°$, only electrons that have passed the plane of the chopper (by approx. ½ d in this example), reach the detector: the chopper appears to close early. By contrast, for large acceptance angles, electrons in a small region before the gate (e.g. $y \geq -0.3$ d for $(KE/V_{app})$ $\theta_{acc}=20°$), still reach the detector and the chopper appears to close late.

Examination of the boundaries for several combinations of $V_{app}$ and $\theta_{acc}$ reveal that, since the deflection is approximately linear in the applied voltage for small deflection angles, the boundaries are a function of the ratio $\theta_{acc}(KE/V_{app})$. Likewise, a scaling argument reveals that, for constant R/d ratio, the trajectories are the same if the electron enters from the field free-region independent of wire spacing, d, as long as the kinetic energy and applied voltage are constant. This implies that the deflection angle is only a function of the ratio $eV_{app}/KE$ for the static chopper potential. Therefore, the information about the boundaries in FIG. 13 summarizes everything that can be known about the time dependant optical properties of the chopper, within the approximation of a single, instantaneous change in chopper potential. Examination of trajectories corresponding to the reverse process, namely electrons approaching the gate with the potential applied and then turned off while in the neighborhood of the chopper, shows that the boundaries are essentially just the mirror image about the plane of the wires and the effects on the time lead or lag mirror the previous case: if for a small acceptance angle the beam turns off early, then it turns on late.

Since the energy corruption depends simply on the position of the electron when the potential is switched, the distribution of energy corruption for a given region of space near the chopper can be extracted simply as a histogram of the potential values (for electrons in the region which reach the detector). As discussed above, we utilize this potential to simulate the effects of energy corruption and lead/lag in beam response on TOF spectra for applications in HREELS.

Thus we have shown that for near unity transmission, trajectory calculations on the potential derived from a conformal map agree well with experimental measurements characterizing both the static deflection and time-dependent response of the chopper, suggesting that this potential is a useful limiting-case description of the interleaved comb device. The finite penetration of the field beyond the plane of the chopper leads to non-ideal chopper response, which is characterized in terms of an energy corruption effect and lead or lag in the time at which the beam responds to the chopper potential.

6. Other Embodiments of the Invention

Alluded to above was the fact that the invention can be applied to other types of spectrometers. One preferred embodiment of the invention for mass spectrometry, for example, is shown schematically in FIG. 14.

In such an instrument, ions must first be created in a source, for example by electron impact, chemical ionization, or electrospray ionization. In electron impact, electrons emitted from a heated filament 300, held at a potential $-V_{fil}$, are accelerated into a cage 304 held at $+V_{ion}$, where ionization of molecules occurs. Ions are then extracted from the cage 304 by a grid 308 of less positive potential, $V_{xtr}$, and then collimated to produce a narrow angular distribution by the collimator slits 310. The beam of ions is either deflected by the "chopper" or modulator 315 (beam "off") or passes undeflected (beam "on"), depending upon the state of the applied voltage at the time the ion approaches the gate. A third collimation slit 318 selects the undeflected ions.

We now turn to optimal operation of the ion gate. We have shown (FIG. 13) that for a given ion energy, there is a critical boundary, characterized by the ratio $(KE/V_{app})\theta_{acc}$, beyond which ions must have passed at the time the potential is turned off for the ion to still reach the detector 320. For a monochromatic ion energy distribution, all ions follow the same trajectory, although at different speeds due to their range of masses. When the critical boundary lies after the plane of the modulator or "chopper" grid 315, the response of the beam to the applied voltage appears to turn off late and turn on early. The lead or lag time is dependent on the particle's velocity, and for a distribution of ions with different masses but the same energy, the lead or lag is mass dependent. However, by choosing the ratio of $K=(KE/V_{app})\theta_{acc}$, so as to place the critical boundary on the plane of the chopper, the lead/lag effects can be minimized. The value illustrated in FIG. 13 corresponds to a radius to spacing ratio of 10, or a nominal grid transmission of 90%. The values of K are easily determined from trajectory calculations for other geometries of the Bradbury-Nielsen gate. To the extent that the extracted ions have a finite energy distribution, the critical boundary is blurred, and the rise and fall times associated with the response of the beam to the chopper 315 will be degraded.

Figure 14:
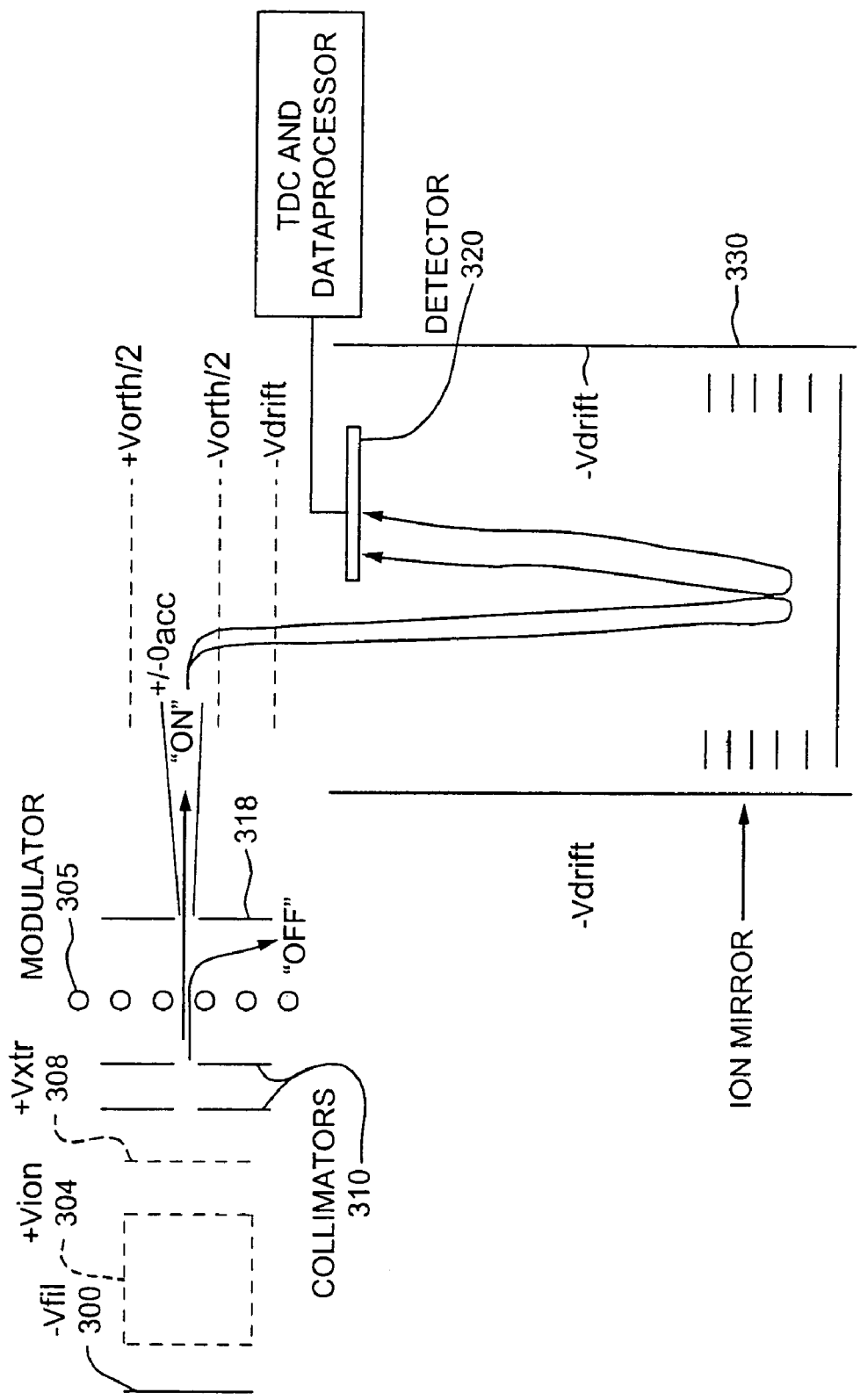
FIG. 14 shows a schematic arrangement of a time-of-flight mass spectrometer according to the present invention.
Figure 15A:
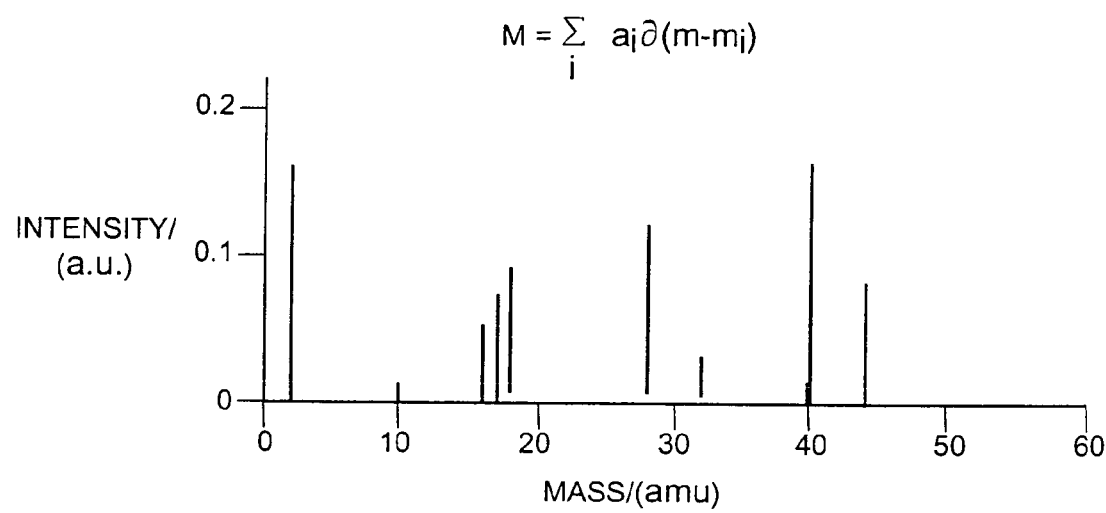
FIGS. 15a–15d illustrate schematically the process steps of a model of the processes occurring in the TOF mass spectrometer of FIG. 14 that can be used in estimating the mass spectrum according to the methods of the present invention.
Figure 15B:
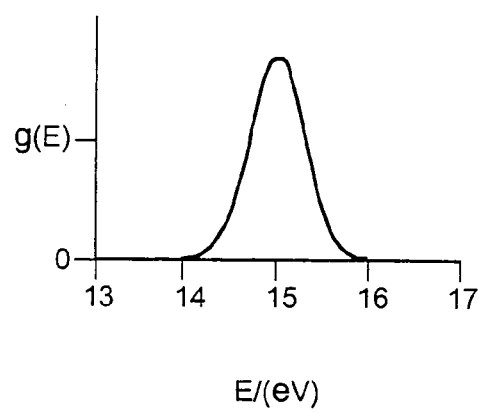
Figure 15C:
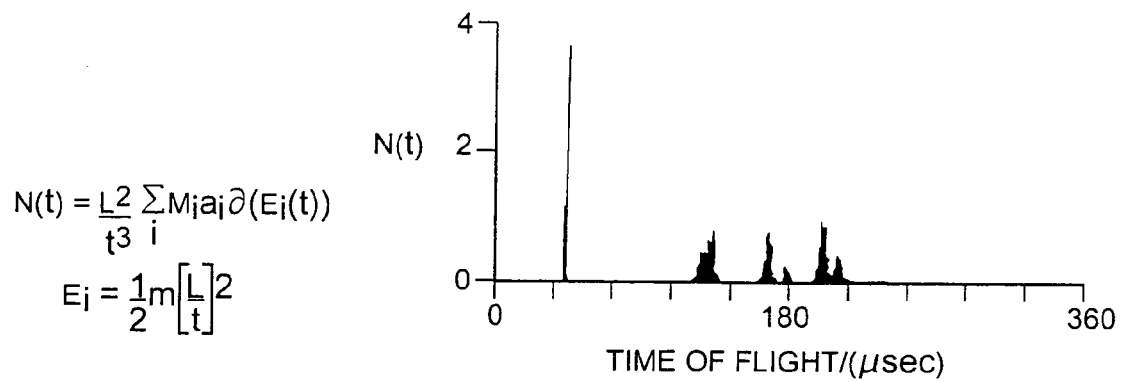
Figure 15D:
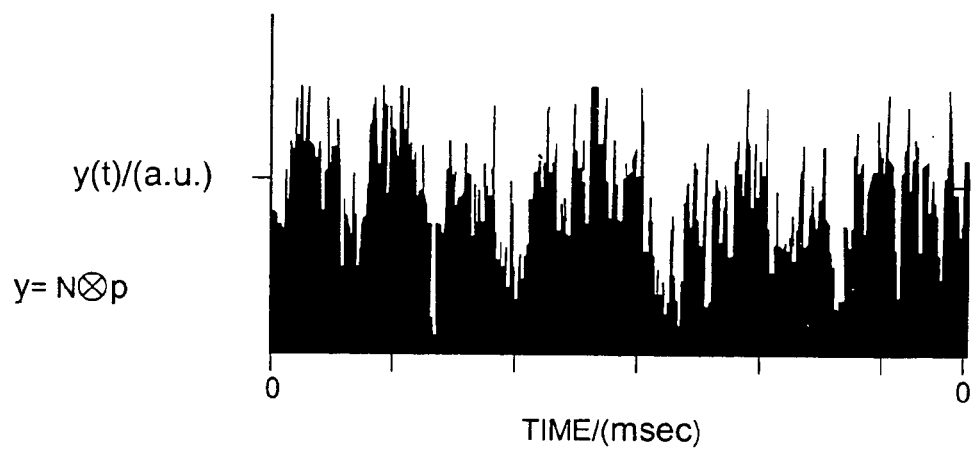

Although the lead or lag can be optimized, the energy corruption effects must be handled in a separate manner. Depending upon the position of the ion at the time the potentials on the gate are switched, the ions will gain or lose energy. However, because the acceptance angle of the collimated beam can be chosen to be small (typically $\leq 1°$), the energy spread is essentially confined to the x-direction. For mass spectrometry applications, it is therefore possible to perform an orthogonal acceleration into a drift tube or a reflectron 330 (FIG. 14). With the simple drift tube geometry, the energy spread in the orthogonal direction, $E_{y+}$, leads to broadening of the TOF spectrum. However, the energy distribution is, to a good approximation, the same for all ions, regardless of mass, and can be accounted for in the statistical recovery model. In the case of a reflectron, the effects of the energy spread are further reduced due to the compensation in arrival time for a properly designed flight tube and ion mirror geometry. The second order aberrations of the reflectron can be corrected with a quadratic potential gradient, which is more complicated to implement in the instrumental hardware. Our method accounts for these aberrations in the statistical model.

FIG. 15 illustrates schematically an algorithm to model the mass spectrum. The possible masses of ions are determined by the isotope masses, and hence can be properly described by a discrete set of delta functions. The possible mass values are fixed; only the intensities are variable. To the extent the ions have the same angular distribution after the collimator, their spatial distribution in the orthogonal acceleration region is similar and the distribution of energies after acceleration to the drift velocity is similar. In the simple drift tube configuration, the spread in the arrival time is mass dependent. However, the energy distribution can be estimated from a calibration standard, such as high purity helium gas. The model therefore consists of calculating the single pulse TOF spectrum based upon the intensities of all possible mass peaks and the common ion energy distribution (more precisely, the $E_y$ component), followed by convolution with the modulation sequence. The optimization therefore consists of adjusting the magnitude of the mass peaks, assuming the shape of the ion energy distribution and the chopper response function have been obtained in previous instrumental calibration steps.

Figure 16A:
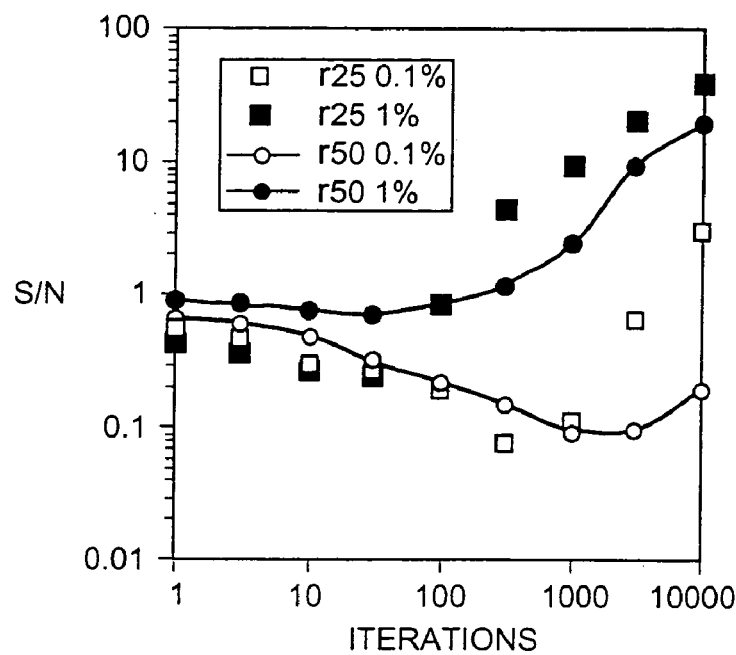
FIGS. 16a and 16b compare the results of using the Lucy algorithm to recover a TOF HREELS-like spectrum when maximal length (ML) and non-ML sequence of varying duty cycle are used for modulation.
Figure 16B:
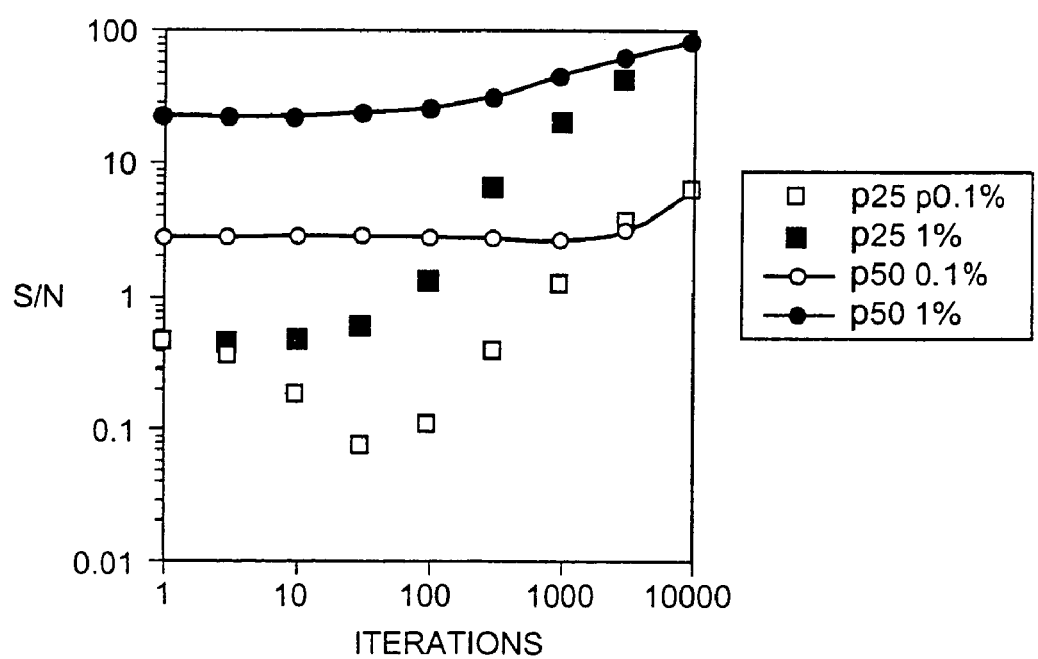

Although the simulation results presented above were for strictly maximal length pseudo random bit sequences (ML-PRBS), the invention has application to other modulation sequences as well. FIGS. 16A and 16B compare the results of such ML sequences with more random, non-ML sequences.

Figure 17A:
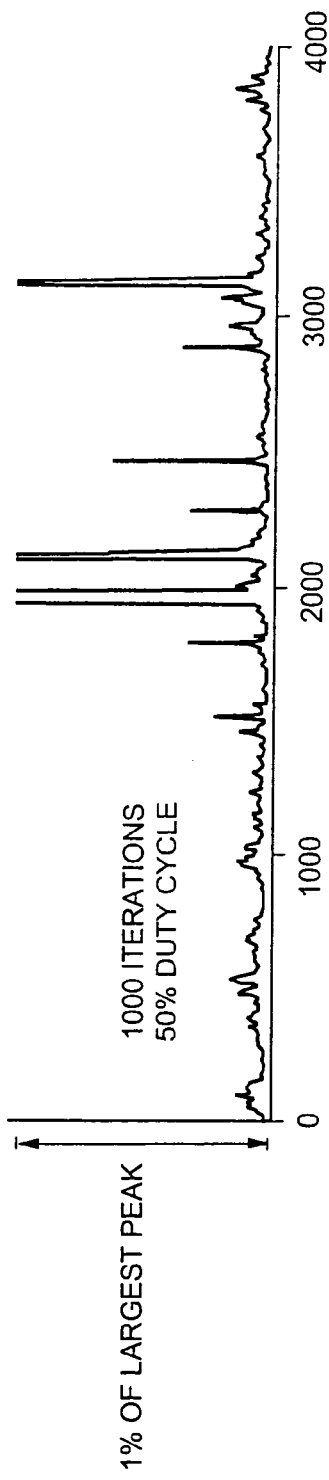
FIGS. 17a–17c compare the true object spectrum (FIG. 17a) with the results of recovering synthetic data with the Lucy algorithm after 1000 iterations when the data was modulated with a randomly chosen set of "1"s and "0"s with a duty cycle of 25% in FIG. 17b and 50% in FIG. 17c.

Object spectra from a TOF instrument were first simulated as shown in the plot of FIG. 17a. The spectra typically consists of several peaks ranging in height down to 0.1% of the largest peak (please note that for the sake of clarity, only the "bottom 1%" of the plot is shown; otherwise the large dynamic range of the dominant spectral line would obscure the artifacts in the plot. An example raw object spectrum is shown in the lowest trace.

Figure 17B:
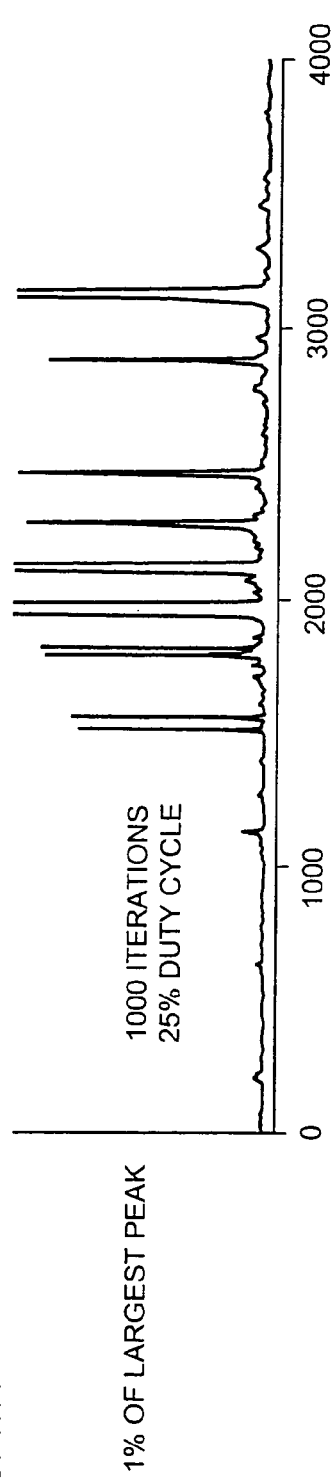

We then applied a non-ML, purely random sequence of bits with a 25% duty cycle as a modulation function for 1000 iterations. By duty cycle, we refer to the fraction of "0"s in a sequence of "0"s and "1"s in the modulation sequence. The spectrum of FIG. 17b then resulted. Note that the line spectra occur in the expected places with little or no artifacts being added.

Figure 17C:
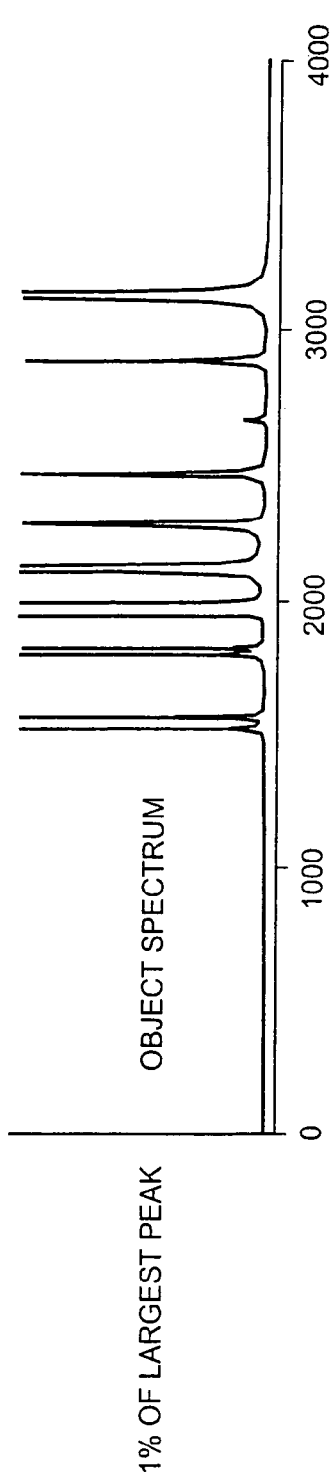

Indeed in another example, shown in the plot of FIG. 17c was the result for a 50% duty cycle. Note the artifact that has been introduced at about 1600 ns, which could result in errors in the interpretation of the results. Apparently then, reducing the duty cycle from 50% can provide advantages.

FIGS. 16a and 16b analyze the results of modulating with four different modulation sequences as a function of the number of iterations using the Lucy algorithm. These included:

a 9 bit maximal length shift register (ML) sequence (length=511 bits)

an 8 bit maximal length shift register sequence (length=255 bits) with three additional zeros inserted at each zero in the sequence to produce a 25% duty cycle sequence with the same length as the 9 bit sequence a random sequence with a 50% duty cycle; and a random sequence with a 25% duty cycle All sequences were over sampled by expanding each bit 8 times to produce a 4088 bit sequence.

To simulate the instrument, the object spectrum was then convoluted with the modulation sequence using an FFT; Poisson noise was also added to data at this point. The spectrum was then recovered from this data using the Lucy algorithm, with various numbers of iterations.

For each recovered spectrum, the largest artifact was determined by examining the parts of the spectrum where there were no known peaks; a signal to noise ratio (S/N) was then calculated for the 0.1% and 1% peaks using the largest artifact as the noise reference level.

The plots show the standard ML sequences gives the highest S/N for a given number of iterations. The plots also show that S/N for a given peak, but different sequences, converges to similar values for large number of iterations. These results illustrate that if a standard ML sequence is not possible or desirable, a non ML sequence can be used without sacrificing S/N. Since ML sequences are well known, non ML sequences may be more desirable for encryption applications. As processing speeds continue to increase, large numbers of iteration become less of a problem. Since the first iteration is the cross correlation of the data with the sequence, the plot shows that Lucy improves the S/N over the cross correlation.

In summary, we conclude that probability based estimation methods recover the most probable result, given the limited information available. The information content is determined by many factors, including the signal to noise ratio, sampling rate, sequence length, sequence frequency content (compare for example the difference between the use of maximal length sequences and the sequence of randomly chosen 1's and 0's), as well as the bandwidth of the system response function and underlying TOF spectrum. Note that if the underlying TOF spectrum has broad, slowly varying peaks compared to the system response function, then the instrument has sufficient resolving power that there is nothing to be gained by deconvolution as far as resolution is concerned, although artifacts may still be produced if the recovery is performed with the cross-correlation method. Conversely, if the TOF spectrum has peak widths that are comparable to or less than the single pulse response function of the system, then the instrument limits the resolution and resolution enhancement is possible.

While this invention has been particularly shown and described with references to preferred embodiments thereof, it will be understood by those skilled in the art that various changes in form and details may be made therein without departing from the scope of the invention encompassed by the appended claims.

What is claimed is:

1. An instrument for analyzing particles comprising:
   a source for a modulated particle beam, the modulated particle beam containing a stream of particles modulated according to a modulation sequence having substantially broadband frequency content;
   a detector for detecting attributes of the modulated particle beam and generating an output signal in response thereto; and
   a processor for recovering information concerning the modulated particle beam from the data output signal using a probability based estimation method which obtains a corrected data output signal, given a system response function, p, that represents a response of the instrument to the broadband binary modulation sequence.

2. An apparatus as in claim 1 wherein a maximum likelihood method is used.

3. An apparatus as in claim 1 wherein a Bayesian method is used.

4. An apparatus as in claim 1 wherein the system response function, p, is obtained from a model of at least one component of the instrument selected from a group consisting of the modulated particle beam source, and the particle detector.

5. An apparatus as in claim 4 wherein the probability based estimation method characterizes noise in the selected component.

6. An apparatus as in claim 5 wherein the noise characterization is selected from a group consisting of Gaussian and Poisson.

7. An apparatus as in claim 1 wherein the information recovery processor is a software program running in a digital signal processor.

8. An apparatus as in claim 1 wherein the results of the information recovery processor are histogrammed.

9. An apparatus as in claim 1 wherein the particle beam is one selected from a group consisting of ions, electrons, neutrons, molecules, and photons.

10. An instrument for analyzing particles comprising:
    a particle beam source providing a continuous beam of particles, the beam having substantially constant flux;
    a modulator for modulating the particle beam by passing it substantially unaltered during on periods, and affecting the beam during off periods according to a binary sequence having substantially broadband frequency content;
    a detector for detecting attributes of the particle beam and generating a measured output signal in response thereto; and
    a processor for recovering information concerning the particle beam from the measured output signal using an iterative probability based estimation method, the probability based estimation method
    i. compensating for non-ideal characteristics of the components of the system by using a system response function, p, that represents a response of the particle beam to a broadband binary modulation sequence; and
    ii. allowing higher resolution to be obtained than a nominal time unit corresponding to a clock period of the modulator would provide without the broadband binary modulation sequence, depending upon at least one of the signal to noise ratio, the oversampling of the time base, and the rise time of the response function.

11. An apparatus as in claim 1 wherein the probability based estimation method is an iterative method.

12. An apparatus as in claim 1 wherein the modulation sequence is a Pseudo Random Binary Sequence (PRBS).

* * * * *